US006855329B1

(12) United States Patent
Shakesheff et al.

(10) Patent No.: US 6,855,329 B1
(45) Date of Patent: Feb. 15, 2005

(54) SURFACE COATING SPATIALLY CONTROLLED PATTERNS

(75) Inventors: Kevin Shakesheff, Derby (GB); Nikin Patel, Nottingham (GB); Scott M. Cannizzaro, Cotuit, MA (US); Robert S. Langer, Newton, MA (US)

(73) Assignees: Massachusetts Institute of Technology, Cambridge, MA (US); The University of Nottingham, Nottingham (GB)

( * ) Notice: Subject to any disclaimer, the term of this patent is extended or adjusted under 35 U.S.C. 154(b) by 0 days.

(21) Appl. No.: 09/600,502

(22) PCT Filed: Jan. 20, 1999

(86) PCT No.: PCT/GB99/00192

§ 371 (c)(1),
(2), (4) Date: Oct. 17, 2000

(87) PCT Pub. No.: WO99/36107

PCT Pub. Date: Jul. 22, 1999

(30) Foreign Application Priority Data

Jan. 20, 1998 (GB) ............................................. 9801061

(51) Int. Cl.[7] ......................... A01N 25/08; A01N 61/90; A01N 43/04; A61F 2/00; C12Q 1/68

(52) U.S. Cl. ........................... 424/409; 424/426; 435/6; 514/1; 514/44

(58) Field of Search ........................ 435/6; 574/1, 44; 424/409, 426

(56) References Cited

U.S. PATENT DOCUMENTS 4,282,287 A    8/1981 Giese ........................... 428/407
5,252,743 A  * 10/1993 Barrett et al. ................ 548/303

FOREIGN PATENT DOCUMENTS

WO     WO 96/40002 A1    12/1996
WO     WO 97/07429 A1     2/1997
WO     WO 97/33737 A1     9/1997

OTHER PUBLICATIONS

Barrera, et al., "Synthesis and RGD peptide modification of a new biodegradable copolymer. Poly(lactic acid co–l–ysine)," *J Am Chem Soc* 115:11010–11011 (1993).
Cook, et al., "Characterization and development of RGD–peptide–modified poly(actic acid–co–lysine) as an interactive, resorbable biomaterial," *Journal of Biological Materials Research* 35:513–523 (1997).
Danielsen, "Nerve regeneration and repair," *Diabetic Medicine* 13:677–678 (1996).
Delamarche, et al., "Patterned delivery of immunoglobulins to surface using microfluidic networks," *Science* 276:779–81(1997).
Hubbell, "Biomaterials in tissue engineering," *Biotechnol* 13:565–76 (1995).
Kumar, et al., "Patterning self–assembled monolayers: Applications in materials science," *Langmuir* 10:1498–1511 (1994).
Langer & Vacanti, "Tissue engineering," *Science* 260:920–927 (1993).
Langer, "1994 Whitaker Lecture: Polymers for drug delivery and tissue engineering," *Annals of Biomedical Engineering* 23:101–111 (1995).

(List continued on next page.)

Primary Examiner—Jezia Riley
(74) Attorney, Agent, or Firm—Pabst Patent Group LLP

(57) ABSTRACT

The invention provides a biodegradable and biocompatible polymer article having a surface wherein a biologically active ligand is provided on said surface in a spatially controlled pattern. The pattern may be formed using a poly(dimethyl siloxane) mold. The biologically active ligand may be attached to the polymer article by a biotin-avidin-biotin linkage.

47 Claims, 12 Drawing Sheets

OTHER PUBLICATIONS

Figure 1:
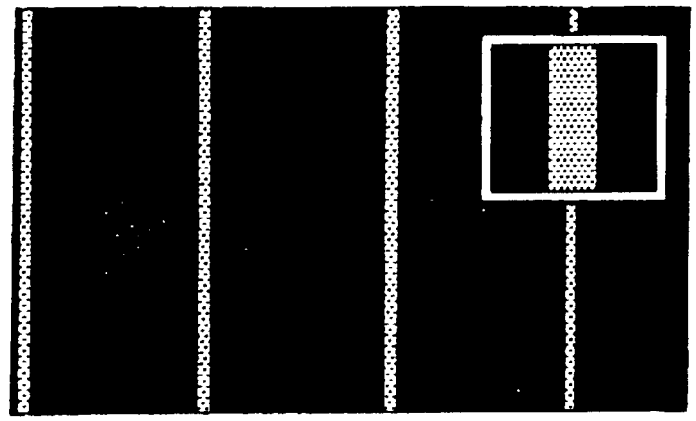
Figure 1:
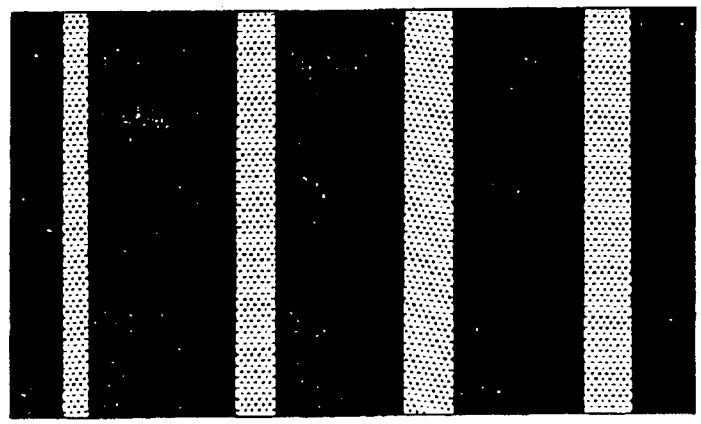

Lhoest, et. al., "A new plasma–based method to promote cell adhesion on micrometric tracks on polystyrene substrates," *J Biomater Sci Polymer Edn* 7(12):1039–1054 (1996).

Mrksich & Whitesides, "Using self–assembled monolayers to understand the interactions of man–made surfaces with proteins and cells," *Annu Rev Biophys Biomol Struct* 25:55–78 (1996).

Pande, et al., "A biotinylated undecylithiophene copolymer bioconjugate for surface immobilization: Creating an alkaline phosphatase chemiluminescence–based biosensor," *Bioconjugate Chem.* 7:159–164 (1996).

Ranieri, et al., "Neuronal cell attachments to fluorinated ethylene propylene films with covalently immobilized laminin oligopeptides YIGSR and IKVAV. II," *Journal of Biomedical Materials Research* 29:779–785 (1995).

Ranieri, et al., "Spatial control of neuronal cell attachment and differentiation of convalently patterned laminin oligopeptide substrates," *Int J Dev Neuorsci* 12(8):725–735 (1994).

Schmidt, et al., "Stimulation of neurite outgrowth using an electrically conducting polymer," *Proc Natl Acad Soc USA* 94:8948–8953 (1997).

Spargo, et al., "Spatially controlled adhesion, spreading, and differentiation of endothelial cells on self–assembled molecular monolayers," *Proc Natl Acad Sci USA* 91:11070–11074 (1994).

Xia & Whitesides, "Extending microcontact printing as a microlithographic technique," *Langmuir* 12:2059–67 (1997).

* cited by examiner

Fluorescence images of patterned surfaces

12 μm wide lines 20, 40, 70 70 μm wide lines

Images of Directed Endothelial Cell Growth

SURFACE COATING SPATIALLY CONTROLLED PATTERNS

Priority is claimed under 35 U.S.C. §119 to PCT/GB99/00192, filed Jan. 20, 1999, which corresponds to GB 9801061.4 filed Jan. 20, 1998.

The present invention relates to a method of generating patterns of biologically active ligands on surfaces.

The use of poly(dimethyl siloxane) moulds to pattern molecules onto surfaces was pioneered by G. M. Whitesides at Harvard University [1, 2]. Materials such as metals, Si/SiO$_2$, glass, non-biodegradable polymers have been used as substrates for patterns [1–3]. The pattern, which may be a self-assembled monolayer (SAM), may be formed, for example, from alkanethiolates on coinage metals, alkylsiloxanes on hydroxyl-terminated surfaces or palladium (Pd) colloids on Si/SiO$_2$. Many of the techniques used have not been adapted to allow peptides, proteins and other biomolecules to be patterned.

Delamarche et al [4] describe a patterning technique to deliver immunoglobulins to surfaces. The technique is described as useful in vitro bioassays, the design of bioelectronic devices and combinatorial screening strategies. The paper does no propose any tissue engineering applications for the technology nor the use of biodegradable surfaces. The patterning technique immobilises complete immunoglobulin molecules by coupling between amino groups in the protein and gold, glass or Si/SiO2 surfaces previously activated by formation of a hydroxysuccinimidyl ester. This may mean that a significant proportion of the immobilised protein is present in an inactive conformation. The mould is exposed to an oxygen plasma prior to contact with the substrate in order to make the mould hydrophilic.

A number of groups have investigated methods of using biomaterials (ie materials that do not induce an adverse response when used in vivo; optionally incorporating biological molecules) in tissue engineering procedures [5–7]. Many of these methods involve immobilizing peptides to surfaces and using these peptides to encourage cell adhesion. A number of studies have patterned peptides or proteins on non-degradable surfaces and used these surface for tissue engineering [8, 9]. However, no one has yet described the immobilization of peptides onto biodegradable material surfaces in spatially controlled patterns.

Schmidt et al [10] describes nerve regeneration using electrically conducting polymer biomaterials. A number of other groups have described the use of polymeric biomaterial as nerve regeneration "bridges". For example, see Danielson (1996) *Diabetic Aled* 13, 677–678. The general approach taken when employing biomaterials has been to form a cylindrical sheath around severed nerve ends. Within this sheath the nerve ends regrow and join to form a complete nerve. The sheath approach does not involve the use of any patterned structure to control the direction of nerve regrowth and the nerve structures that can be treated by this method are large bundles containing 10's to 100's of neurones.

WO96/40002 describes the use of solid free-form fabrication methods in the formation of vascularised tissue regeneration matrices which may be formed from biodegradable materials and may provide controlled release of bioactive agents.

The present invention relates to a process of generating micron-scale patterns of biologically active ligands on biodegradable and biocompatible article surfaces. The patterned biodegradable articles may be employed as tissue regeneration templates. The invention may employ a nanotechnology approach in which molecular interactions between the cells, for example neurons, and a biologically active ligand, for example a peptide, pattern encourage directional cell growth, for example neurite extension. Surfaces may be prepared, for example, that possess narrow lines of peptide molecules, as shown in the fluorescence images in FIG. 1. On these templates, human or other tissue may be encouraged to grow along the lines of peptides or other ligand (FIG. 2). A very wide range of pattern designs may be formed using this technology.

A first aspect of the invention is a biodegradable and biocompatible article having a surface wherein a biologically active ligand is provided on said surface in a spatially controlled pattern wherein the biologically active ligand is attached to the said surface by means of a specific molecular interaction.

A second aspect of the invention is a biodegradable and biocompatible article having a surface wherein a biologically active ligand is provided on said surface in a spatially controlled pattern wherein a dimension of a feature of the said pattern is less than or equal to about 200 μm or 100 μm.

A third aspect of the invention is a biodegradable and biocompatible article having a surface wherein a biologically active ligand is provided on said surface in a spatially controlled pattern wherein the ligand is a nerve or epithelial growth factor or a peptide that may stimulate neurite growth.

By "biodegradable material" is meant that the material dissolves or is broken down or fragmented within a period that is acceptable in the desired application and is less than or about five years, preferably between one hour and five years, more preferably between one day and one year, still more preferably between one week and one year. The material should also be biocompatible, which means that the material and its degradation products are not unacceptably immunogenic, allergenic or toxic. The rate of dissolution or degradation is measured on exposure to a physiological saline solution of pH 6.0–8.0 having a temperature of between 25 and 37° C., for example, pH 7.0 at 30° C. Degradation times mentioned below refer to this method of testing. The degradation times are those taken for the sample to substantially disappear. It will be appreciated that the size and shape of the sample may have some influence on the degradation rate and that tests may preferably be carried out with samples of a similar shape and size to those intended to be used in practice. The influence of size and shape is significant for no biodegradable materials that undergo surface erosion. These materials erode (degrade) from the surface only and therefore the surface area of any device (article) will determine the rate of removal of biomaterial. Surface eroding polymers include those of the polyanhydride and poly(ortho ester) classes. Most other biodegradable polymers are bulk eroding (ie degradation occurs throughout the polymer article, not just at the surface), including the lactic acid and glycolic acid based polyesters.

Alternatively, the degradation rate may be measured in vivo as described, for example, in WO 93/16687, wherein a sample of the material to be tested is implanted in the peritoneal cavity of a mouse and explanted after a period of time (for instance up to 8 weeks after implantation). The sample is weighed and mechanical strength may also be tested, as described. Stability over periods longer than 8 weeks cannot be tested using this method.

It will be appreciated the FEP (fluorinated ethylene propylene) and PP (oxidised polypyrrole), for example, are not biodegradable materials as defined above.

Polymers of polyhydroxy acids including polyhyroxybutyric acid, lactic, glycolic and ε-caproic acid, polyhydrides, polyorthoesters, polyphosphazenes, polyphosphates, polycaprolactone or copolymers prepared from the monomers of these polymers can be used (see for example WO 95/03357). Biodegradable hydrophobic polyanhydrides are disclosed in, for example, U.S. Pat. Nos. 4,757,128, 4,857;311, 4,888,176 and 4,789,724. Polyhydroxybutyrates are disclosed in U.S. Pat. No. 3,044,942. Polymers of lactic acid or glycolic acid, or copolymers of these monomers are preferred. Block copolymers of the above polymers, preferably polylactic acid, polyglycolic acid or poly(lactic-co-glycolic)acid and poly(alkylene glycol), for example poly(ethylene glycol) (PEG) may be particularly suitable.

Suitable synthetic biodegradable polymers are set out in list form below:
1. Polyesters Including: poly(lactic acid)

poly(glycolic acid)

copolymers of lactic and glycolic acid copolymers of lactic and glycolic acid with polyethylene glycol)

poly(ε-caprolactone)

poly(3-hydroxybutyrate)

poly(p-dioxanone)

polypropylene fumarate)
2. Poly(ortho esters)

Including: Polyol/diketene acetals addition polymers as described by Heller ACS Symposium Series 567, 292–305, 1994.
3. Polyanhydrides Including: Poly(sebacic anhydride) (PSA) poly (carboxybiscarboxyphenoxphenoxyhexane) (PCPP) poly[bis(p-carboxyphenoxy) methane] (PCPM)

copolymers of SA, CPP and CPM

Described by Tamada and Langer in Journal of Biomaterials Science Polymer Edition, 3, 315–353, 1922 and by Domb in Chapter 8 of the Handbook of Biodegradable Polymers, ed. Domb A. J. and Wiseman R. M., Harwood Academic Publishers.
4. Poly(amino acids)
5. Poly(pseudo amino acids)

Including those described by James and Kohn in pages 389–403 of Controlled Drug Delivery Challenges and Strategies, American Chemical Society, Wash., DC.
6. Polyphosphazenes Including: derivatives of poly[(dichloro) phoisphazene] poly[(organo) phosphazenes] polymers described by Schacht in Biotechnology and Bioengineering, 52, 102–108, 1996.

Polysters may be the polymer system of choice for a commercial embodiment.

In a preferred embodiment polyesters of poly(lactic-co-glycolic)acid (PLGA) are used. These polymers are approved for parenteral administration by the FDA. Because PLGA degrades via non-enzymatic hydrolysis in the initial states, in vivo degradation rates can be predicted from in vitro data. PLGA degrades to lactic and glycolic acids, substances found naturally in the body.

When the polyester material has broken down to molecular weights of about 5000 Daltons, the material may be taken up by cells, including macrophages, so some inflammation may be associated with the breakdown of these polymers.

Copolymers with polyalkylene glycol, for example PEG, reduce the level of inflammation seen. Copolymers comprising a polyalkylene glycol are preferred to those without polyalkylene glycol. The polyalkylene glycol also helps to reduce non-specific protein absorption. To ensure elimination from the body, the PEG should have a molecular weight of between approximately 300 and 20,000 Daltons. The rate of hydrolysis is also increased for copolymers containing a biodegradable component with polyalkylene glycols.

Water soluble copolyester prepolymers with polyethylene glycol may be used as precursors to form hydrolytically degradable hydrogels. Hydrogels such as these may be particularly useful. The polyester may be present as an oligomer at the termini of the polyethylene glycol and since the polyester concentration in the swollen hydrogel is very low, inflammation may be substantially absent during degradation. Other copolymers which may be suitable include a block copolymer of polyethylene glycol with polypropylene glycol, known as Pluronic™ or Poloxamer™ surfactants. These are soluble in cold water, but form a hydrogel at 37° C.

It will be appreciated that a cross-linked hydrogen may be preferred. The cross-linking may further stabilise the hydrogel and any pattern present on its surface.

Copolymers with amino acids may be synthesised, for example glycolic acid and glycine, or lactic acid and lysine (Barrera et al (1993) J. Am Chem Soc 115, 11010–11011 and Cook et al (1997) J Biomed Mat Res 35, 513–523). These may be useful for immobilizing other molecules, for example via the lysyl ε-amino moieties. These polymers may be used to attach peptides to surfaces using covalent bonds. For example, peptides may be attached to poly (lactic acid-co-lysine) using 1,1'-carbonyl-diimidazole (CDI, Aldrich) as a linking agent as described in the above references.

By manipulating the molar ratio of lactic and glycolic acid and the molecular weight of the copolymers, different degradation patterns can be obtained. Poly-L-lactide as a degradation time in vitro of months to years. The long degradation time is due to its high crystallinity which protects the polymer from water penetration. Poly-glycolide has a degradation time of one to several months, whereas poly-DL-lactide is amorphous and has a degradation time in vitro of weeks to months. D,L-PLGA has a degradation time in vitro of weeks to months. As the glycolic acid ratio is increased, the rate of degradation increases. Homopolymers of ε-caproic acid can remain intact for 2–3 year periods of implantation.

It will be appreciated that the degradation time of a polymer may be altered when other molecules, for example biotin, are incorporated. PLA-PEG-biotin is a biocompatible, biodegrable solid polymer with amphiphilic properties that generate a hydrophilic surface region that is particularly preferred in embodiments of the invention.

Other biodegradable materials include collagen (fibrillar or non-fibrillar forms) and polysaccharide gels, for example hyaluronic acid. Copolymers of collagen and proteoglycans may be used. Chemical crosslinking with glutaraldehyde may be employed to manipulate the stability and rate of resorbtion of the matrix. Hyaluronic acid may be altered by chemical modification, for example esterification which alters its hydrophilicity. Protein polymers may also be prepared by molecular biology techniques.

For example, polymers based on silk or elastin repeating units may be prepared, as reviewed in [5] and are suitable for use in the present invention. Biotin may be covalently incorporated into such molecules.

It will be appreciated that some biocompatible polymers, for example some natural polymers as described above, may degrade in response to cellular activity. This is referred to as removal or degradation by metabolism. In particular, gels may be degraded by specific proteases produced by cells. Thus, the rate of degradation may reflect the rate of tissue regeneration and may vary depending on the tissue involved. It will be appreciated that non-enzymic degradation (for example hydrolysis) and metabolic degradation may both contribute to the degradation of a biodegradable material.

By "patterned" is meant that,the density of immobilized molecule (ligand) varies over the surface of the substrate (article) in a substantially predefined manner. Preferably the immobilized molecules are substantially absent from at least one region of the surface and are present in a biologically effective amount in at least one other region of the surface.

It is preferred that the boundaries of the said regions are well defined. Thus, it is preferred that the transition from presence in a biologically effective amount to substantial absence occurs over a distance that is less than all, ¾, ½, ¼⅕ or ⅒ of the smallest dimension of a feature of the pattern (measured substantially in the plane of the surface). Thus if the pattern can be observed, for example using an appropriate microscopic technique, as discussed below, the regions may appear to have sharp edges.

Thus a simplest patterned surface may be one where one pre-defined region of the surface has substantially none of the ligand immobilised on it and a second pre-defined region has an effective amount of the ligane effectively immobilised on it.

Figure 2:
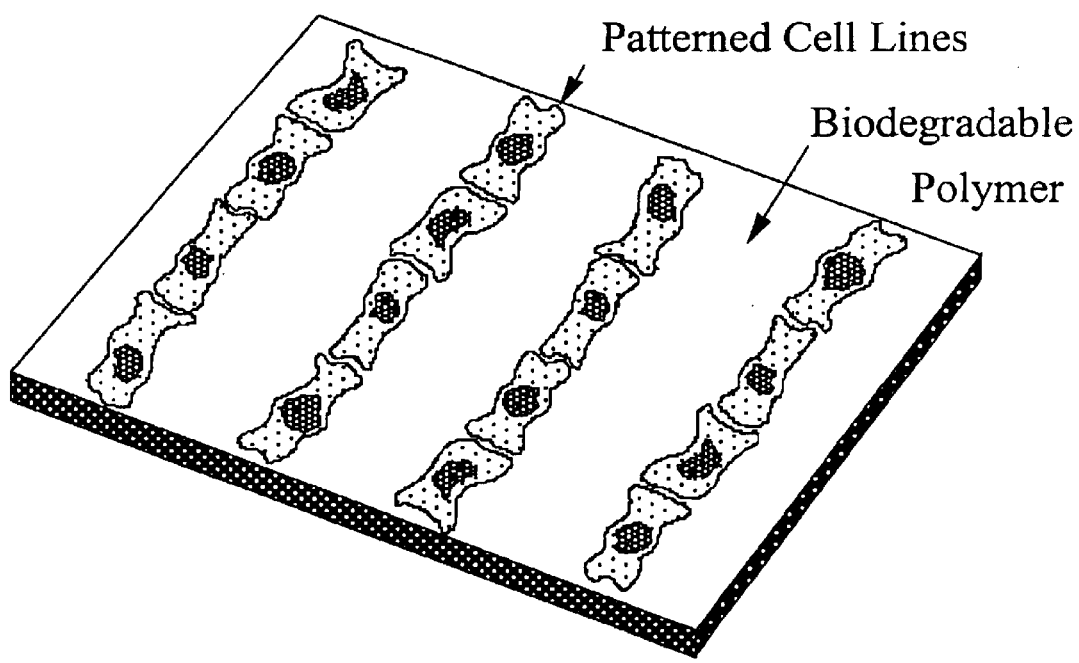

A preferred pattern may be lines, as shown in FIG. 1. It is preferred that the dimensions of the lines are such as to be effective in guiding the growth of cells such as to form the desired tissue structure. The appropriate dimensions for a particular situation may be determined by, one skilled in the art. Particularly preferred line widths may be 12, 20, 40 or 70 $\mu$m. The most useful line widths may be between 100 nm and 1 mm, preferably between 10 and 100 $\mu$m or 200 $\mu$m (determined by the width of the cell type to be engineered—it may be preferred that the line width is similar to that of the cell type). It is further preferred that a dimension of a feature of the said pattern is less than or equal to about 1 mm, 200 $\mu$m, 100 $\mu$m, 10 $\mu$m, 1 $\mu$m or 100 nm. It is still further preferred that a dimension of a feature of the said pattern is less than or equal to about 90 $\mu$m, 80 $\mu$m, 70 $\mu$m, 60 $\mu$m, 50 $\mu$m, 40 $\mu$m, 30 $\mu$m, 20 $\mu$m, 10 $\mu$m. 1 $\mu$m, 500 nm or 100 nm. It will be appreciated that the said dimension is measured substantially in the plane of the patterned surface and is not the dimension substantially perpendicular to the said surface.

It will be appreciated that the said dimension may be determined more readily when the boundaries of the said feature are clearly defined. The dimension may be measured, for example, across a region that has an effective amount of the ligand effectively immobilised on it, between points abutting the said region at which the biologically active ligane is, for example, substantially absent. If the boundaries of the feature are irregular, for example if a feature is formed from multiple subfeatures, for example by the deposition of discrete or overlapping droplets, then a dimension may be calculated as a dimension of the region enclosed by a smooth curve that contacts the outward-facing boundary of each subfeature.

It will be appreciated that the said dimension may be determined by examination of the pattern, for example using a microscope to examine a pattern of a fluorescent marker molecule, for example as described below for the detection of patterns of fluorescein isothiocyanate-labelled avidin. Atomic force microscopy may be used as described in Example 7. Alternatively, the said dimension may be determined from the dimensions of the appropriate part of a device used to form the pattern, for example, the size of a raised or a recessed portion of a mould or stamp, as discussed below, or the calculated size of a droplet dispensed in an ink-jet style printing process, as discussed further below.

It will be appreciated that the length of the lines will be determined by the dimensions of the tissue to be regenerated, but may be up to 1 cm, or more preferably 5 cm. The length of the lines may be between 100 $\mu$m and 50 cm depending on the application. For example neurogenesis may involving linking two nerve ends over a distance of 100 pm or linking a nerve to a distant tissue.

The lines may be substantially parallel. Other patterns that may be of use include branching patterning in which a line splits into two or more branches, each of which may split into two or more branches. This branching may occur several times such that a "tree" pattern is formed. It is preferred that a line is split n times, where n may be 1, 2, 3, 4, 5 or more.

The surface may have any shape. It may be, for example, flat, curved or tubular.

It will be appreciated that the pattern may be three-dimensional. Thus, the pattern may comprise features, for example ridges or tubes, of the same or different biodegradable and biocompatible polymer to the supporting surface, on which the biologically active ligand may be present at a different density. Such a three-dimensional pattern may be formed using a mould, as described further below. It will be appreciated that a surface maybe patterned with more than one type of biologically active molecule. This may be of particular benefit in regenerating hepatic tissue where the vascular structure is important for the function of the regenerated tissue. Patterning of more than one type of molecule may be achieved by sequential patterning of the different types of molecule or by application of the different types to different parts of the surface essentially simultaneously.

By biologically active molecule is meant any molecule that may have an effect on a biological process. It is preferred that the effect is to influence the growth or differentiation of cells. It will be appreciated that the biologically active molecule may inhibit or promote growth and/or differentiation of a particular type of cell. It is preferred that the biologically active molecule is a peptide, protein, carbohydrate, nucleic acid, lipid, polysaccharide, or combinations thereof, for example a proteoglycan, or synthetic inorganic or organic molecule. It is particularly preferred that the biologically active molecule is a peptide, preferably consisting of one or more of the twenty commonest naturally occurring amino acids, having 2 to 1000 or more, preferably 5 to 100 residues.

It is preferred that the biologically active molecule is able to exhibit its activity whilst bound to the biodegradable surface. However, it will be appreciated that the molecule may also be one that may be slowly released from the biodegradable surface and exhibits its activity when so released. Further, a second molecule type (for example a growth hormone) may be fixed to the surface (but not necessarily in a pattern as defined above), and then released. As an alternative, the second molecule type may be implanted into the bulk of the polymer and then released.

It is preferred that the biologically active molecule is a ligand for a cell surface receptor. It is particularly preferred that thee molecule is a ligand for a receptor belonging to the integrin family of receptors, reviewed for example in Hynes (1992) "Integrins: versatility, modulation and signalling in cell adhesion" Cell 69, 11–25. Examples are receptors for fibronectin or vitronectin.

The term "ligand" will be used to denote the biologically active molecule that is to be immobilised.

Examples of ligands that may be used include adhesion proteins, for example fibronectin and vitronectin, or fragments thereof, that are recognized by cytoskeletally associated receptors in the cell membrane, known as integrins. The receptors bind into a small domain on the adhesion proteins, for example the peptide sequence RGD, which is found in many adhesion proteins, and binds to many integrins. Varying the sequence or flanking sequences can alter the binding affinity of a receptor for the peptide or protein containing it. The density of the ligand may affect the cellular response, and it will be appreciated that it may be necessary to control the density of the ligand, for example RGD peptide, to get the optimum density for cell spreading.

A further example is the peptide sequence YIGSR (SEQ ID NO:1), found in laminin (B1 chain) which binds to the 67 kDa laminin receptor found on any cell types. The peptide sequence. IKVAV (SEQ ID NO:2) is found on the A chain of laminin and binds the 100 kDa receptor and may induce neurite growth. This peptide is not significantly water soluble, and the water soluble peptide CSRARKQAASIKVAVSADR (SEQ ID NO:3) may be used instead. REDV (SEQ ID NO:4) (from fibronectin) binds to the integrin on human endothelial cells, but does not support adhesion or spreading of smooth muscle cells, fibroblasts or platelets and may therefore be useful for achieving selective cell adhesion.

Many different peptides that contain the IKVAV (SEQ ID NO:2) sequence may stimulate neurite extension. Any peptide that comprises a sequence of amino acids that is able to bind to a cell adhesion receptor may be used. The suitability of a peptide may be assessed by a means of measuring protein-protein interactions, as known to those skilled in the art. Suitability may also be assessed by functional assays, for example assessing the growth of a cell type of interest on a surface patterned with the peptide under consideration.

Still further examples include epidermal growth factor (EGF), nerve growth factor, insulin-like growth factor (IGF), basic fibroblast growth factor (bFGF), platelet derived growth factor (PDGF), transforming growth factor-β and related growth factors, for example bone morphogenetic proteins (BMPs), cytokines including interferons, interleukins, monocyte chemotactic protein-1 (MCP-1). It will be appreciated that these growth factors may also usefully be implanted/incorporated in the biocompatible, biodegradable material and released as the material degrades.

Further examples may include dopamine, amine-rich oligopeptides, such as heparin binding domains found in adhesion proteins such as fibronectin and laminin, other amines and single basic amino acids, or monosaccharide binding to the asialoglycoprotein receptor on hepatocytes. For example, one can immobilise N-acetylglucosamine or lactose or polymerisable N-acetyllactosamine monomer, which can be polymerised to form an adhesive substrate. The sialyl Lewis X saccharide (Varki (1994) "Selectin Ligands" PNAS USA 91, 7390–7397) may be immobilised. It is a ligand for the selectin class of saccharide-binding receptors (Lasky (1992) "Selectins: interpreters of cell-specific carbohydrate information during inflammation" Science 258, 964–969), which are usually responsible for mediating cell-cell interactions. Thus this saccharide may be useful for mimicking cell-cell recognition.

Bone morphogenetic proteins (BMPs) may be useful for closure of defects in bone and basic fibroblast growth factor bFGF useful in inducing a vascularisation response. Slow release formulation, wherein the biologically active molecules are slowly released from the degrading polymer may be effective for these molecules.

TABLE 1

Cell binding domain sequences of extracellular matrix proteins

| Protein | Sequence | Role |
| --- | --- | --- |
| Fibronectin | RGDS (SEQ ID NO:5) | Adhesion of most cells, via αβ receptor |
|  | LDV | Adhesion |
|  | REDV (SEQ ID NO:4) | Adhesion |
| Vitronectin | RGDV (SEQ ID NO:6) | Adhesion of most cells, via αβ receptor |
| Laminin A | LRGDN (SEQ ID NO:7) | Adhesion |
|  | IKVAV (SEQ ID NO:2) | Neurite extension |
| Laminin B1 | YIGSR (SEQ ID NO:1) | Adhesion of many cells, via 67kDA laminin receptor |
|  | PDSGR (SEQ ID NO:8) | Adhesion |
| Laminin B2 | RNIAEIIK DA (SEQ ID NO:9) | Neurite extension |
| Collagen I | RGDT (SEQ ID NO:10) | Adhesion of most cells |
|  | DGEA (SEQ ID NO:11) | Adhesion of platelets, other cells |
| Thrombospondin | RGD | Adhesion of most cells |
|  | VTXG (SEQ ID NO:12) | Adhesion of platelets |

After [5]

TABLE 2

Proteoglycan binding domain sequences of extra-cellular matrix proteins.

| Protein | Sequence |
| --- | --- |
| XBBXBX (SEQ ID NO:13) | Consensus sequence |
| PRRARV (SEQ ID NO:14) | Fibronectin |
| YEKPGSPPREVVPRPRPGV (SEQ ID NO:15) | Fibronectin |
| RPSLAKKQRFRHRNRKGYRSQRGHSRGR (SEQ ID NO:16) | Vitronectin |
| RIQNLLKITNLRIKFVK (SEQ ID NO:17) | Laminin |

After [5]. X indicates a hydrophobic amino acid. Basic amino acids are shown underlined.

By a "specific molecular interaction" is meant an interaction with a $K_d$ of between $10^{-10}$ and $10^{-17}$M, preferably between $10^{-13}$ and $10^{-16}$ M. It is preferred that the component interacts with at least 100-fold higher affinity (and preferably at least 500-fold, or at least 1000-fold, or at least 2000-fold higher affinity) with the intended binding component than with other molecules that may be encountered by either of the said components, for example in tissue culture or when administered to a patient. Thus, the component may interact with at least 100-fold higher affinity (and preferably at least 500-fold, or at least 1000-fold, or at least 2000-fold higher affinity) with the intended binding component than with components of a tissue culture medium, for example Dulbecco's modified Eagle's medium (DMEM), or human or bovine serum albumin.

For the second and third aspects of the invention, the ligand may be immobilised by any means compatible with the biocompatible, biodegradable material and ligand. Such means may include covalent attachment, adsorption or physical entrapment methods similar to those used with non-biodegradable materials, but it will be appreciated that known methods useful with non-biodegradable materials are generally unsuitable for use with most biodegradable materials. Hence, for all aspects of the invention it has been desirable to devise novel means of immobilising a ligand on a surface in order to facilitate immobilisation of a ligand on the surface of a biocompatible, biodegradable article. It will be appreciated that the novel means are particularly desirable in forming a spatially controlled pattern of a ligand on the surface of a biocompatible, biodegradable article.

It is preferred for all aspects of the invention that the biologically active ligand is attached to the said surface by means of a specific molecular interaction, more preferably a specific molecular interaction that has a $K_d$ between $10^{-13}$ and $10^{-16}$. Still more preferably, the specific molecular interaction is between biotin and avidin or streptavidin. The specific molecular interaction may alternatively be, for example, between an antibody or antibody fragment (or other immunoglobulin specific recognition domain) and its antigen, which may be a hapten.

In a preferred embodiment, an "anchor-adapter-tag" system may be used, in which an adapter which can interact specifically and with high selectivity with an anchor molecule (present on the biodegradable surface) and a tag (bound to the ligand to be immobilised) simultaneously is used in attaching the ligand to the surface in a manner which is stable in vivo. This has the advantage that the ligands may be presented in an active conformation, may be attached to the surface in an aqueous environment and may be attached rapidly to the surface. It will be appreciated that the anchor-adapter-tag system may allow the ligand to assume an active conformation, whereas this may be difficult to achieve using other methods of attachment for example adsorption following application to the surface by inkjet style printing. Further, the anchor-adapter-tag system may aid in forming patterned features that have a uniform height (ie measured perpendicular to the supporting material), determined by the dimensions of the anchor, adapter, tag and ligand. This uniform height may aid cell adhesion and growth. A wide range of ligands may be used.

By "high affinity" is meant an interaction with a $K_d$ of between $10^{-13}$ and $10^{-16}$ M. By "interacts specifically" is meant that the component interacts with at least 100-fold higher affinity (and preferably at least 500-fold, or at least 1000-fold, or at least 2000-fold higher affinity) with the intended binding component that with other molecules that may be encountered by either of the said components, for example in tissue culture or when administered to a patient, as discussed above.

It will be appreciated that the said specific molecular interaction required in the first aspect of the invention may occur between a component of the surface and the biologically active ligand molecule (which may, for example, be a fusion molecule, for example with a biologically active domain and a domain that interacts with the said component of the surface). Alternatively, for example, it may occur between a component of the surface and an adapter molecule, as described above, and/or between the said adapter molecule and the biologically active ligand molecule or a tag attached thereto.

It will be appreciated it is necessary only that a biologically active ligand molecule is attached to the said surface by means of one specific molecular interaction; any other molecular interactions involved need not be specific molecular interactions. However, it will be appreciated that it may be preferred that if more than one molecular interaction is involved per ligand molecule, then more than one of the said molecular interactions may be a specific molecular interaction. Thus, the interaction between the surface and an adapter, and between the said adapter and a tag, may, but do not have to, both be specific molecular interactions. The adapter may comprise more than one component, such that a chain of components links the ligand to the surface; each interaction may, but does not have to, be a specific molecular interaction.

It will be appreciated that an adapter molecule, for example, may be able to form specific molecular interactions with more than one molecule, or more than one type of molecule. For example, the adapter may have a specific molecular interaction with an anchor molecule and a further specific molecular interaction with a tag molecule; the anchor and tag molecule may be the same chemical entity, for example biotin, or may be different.

It will be appreciated that, once the said ligand is attached to the said surface in a spatially controlled pattern by means of a specific molecular interaction, a covalent bond may be formed such that the said specific molecular interaction may no longer be required in order for the said ligand to remain attached to the said surface. The said covalent bond may form spontaneously after the specific molecular interaction has taken place, or it may require catalysis. It will be appreciated that such a covalent bond may form between the molecules that participate in a specific molecular interaction, for example between an anchor molecule and an adapter molecule, or between other molecules, for example between the biologically active ligand and a molecule present on the said surface that does not form a specific molecular interaction with the ligand. In a particularly preferred embodiment, the anchor and the tag are biotin and the adapter is avidin or streptavidin. The valency of biotin is one, and that of streptavidin or avidin is 4. The $k_d$ for the binding of biotin to straptavid/avidin is about $10^{-15}$M. This binding is far stronger than many non-covalent interactions, for example antibody/antigen interactions. This system therefore provides an extremely high affinity and long lasting binding.

Any multivalent adapter molecule with the necessary binding affinity may be used. For example, a hapten may be used as the anchor and the same or a different hapten used as the tag, with an antibody of the requisite specificity/specificities used as the adapter. An antibody or antibody fragment may also be used as an anchor or a tag molecue. In this case, the adapter molecule comprises epitopes for the anchor and/or tag, as appropriate. However, the biotin-avidin/streptavidin system may be the easiest and cheapest system. Patterning with antibodies would be performed using a protocol essentially identical to a protocol for the avidin/biotin system.

An anchor molecule such as a protein, for example an antibody or antibody fragment, may be covalently bound to a block copolymer containing a polyalkylene glycol by reaction with the terminal hydroxyl group of the polyalkylene glycol. For example, the hydroxyl group can be reacted with a terminal carboxyl group or terminal amino group on the molecule to form an ester or amide linkage. Alternatively, the molecule can be linked to the polyalkylene glycol through a difunctional spacing group such as a diamine or a dicarboxylic acid. The reaction should be done under conditions that will not adversely affect the biological activity of the molecule being covalently attached to the copolymer.

The polymer may comprise biotin. This allows the ligand to be bound to the polymer by means, of a biotin/avidin link or biotin/streptavidin link. It will be appreciated that the polymer, may comprise a high affinity ligand for a different compound wherein the binding affinity of the ligand for the associated compound is sufficient that a stable interaction is possible in vivo. For example an antibody/hapten pair may be used. For example, the anchor (eg biotin or the hapten) may be covalently attached to the polymer during the synthesis of the polymer (or as a secondary modification of a natural or synthetic polymer) prior to the patterning. In addition, the tag (eg biotin or hapten or any other tag) is attached to the ligand. An aqueous solution of the adaptor is flowed through the capillaries of the mould. Then, after washing and removal of the mould, the modified and patterned polymer surface is incubated in an aqueous solution of the tagged ligand. Suitable polymers include poly(actic acid)-co-poly(ethylene glycol)-biotin (PLA-PEG-biotin). Biotin is incorporated into the polymer by attaching the biotin to the end group of the PEG (polyethylene glycol) block of the PLA-PEG polymer.

A typical synthesis for the production of the biotin containing PLA-PEG diblock polymer is as follows: First, α-amine ω-hydroxy PEG (Shearwater Polymers, Inc., avg. mol. wt. 3.8 k) was stirred with NHS-biotin (Fluka, Milan, Italy) and triethylamine in dichloromethane and acetonitrile at room temperature under argon overnight. The biotinylated PEG was then isolated by vacuum filtration, and dried from toluene azeotrope. Secondly, (l-)lactide was then polymerized from the ω-hydroxy PEG-biotin in refluxing toluene, optionally using stannous 2-ethylhexanoate as a catalyst to give PLA-PEG-biotin. The final polymeric material was recovered by dissolution in dichloromethane and precipitation in cold ether, for example by the addition of cold ether. $^1$H—NMR at each stage confirms the attachment of biotin to the PEG chain. Specifically, attachment of biotin-NHS to the end group amine of α-amine ω-hydroxy PEG to form an amide bond, was confirmed by shift of the, free amine protons to an amide proton at 7.8 ppm and the appearance of a triplet (methylene from biotin arm alpha to the amide) at 2.05 ppm. The proton signals from the biocyclic biotin structure owing to the (2)methine protons (4.5 and 4.2 ppm) and urea protons (6.45 and 6.35 ppm) can be seen throughout the systhesis of PLA-PEG-biotin: the biotin structure remains intact and is not damaged from the latide polymerisation onto HO-PEG-biotin. The preservation of the biotin struction during the synthesis of PLA-PEG-biotin may be verified by $^1$H—NMR and the avidin binding ability of the thered biotin may be confirmed by surface plasmin resonance analysis (Cannizzaro et al (1998) *Biotechnol Boengin* in the press). Also, (l-)lactide monomer feed ratios corresponded to to $^1$H NMR integrations for PLA signals as versus PEG signal indicating efficient converstion of the lactide monomer to PLA. Polymer molecular weights were determined from $^1$H—NMR using the PEG signal as a reference. Gel permeation chromatography revealed one peak indicative of pure material. Polymer molecular weight could be varied from lactide feed ratios. The average PLA molecular weight for this study was 9.2 k. In a similar fashion, the control material, PLA-PEG, was prepared from the monofunctional α-methoxy ω-hydroxy PEG (Shearwater Polymers, Inc., avg. mol. wt. 3 k).

Ways of forming the patterns are described below and may include the following situations:

1. The ligand is able to bind directly to the biodegradable, biocompatible surface without an adapter and the pattern is applied by printing, for example inject style printing.

2. The ability of the biodegradable, biocompatible surface to bind the ligand may be altered by eg phototreatment, laser patterning, doping surfactant treatment (an example of inverse patterning)or removal of a coating, for example using inkjet style printing.

It will be appreciated that the pattern of biologically active ligand is formed directly on a surface of biodegradable, biocompatible material. It is not formed on a nonbiodegradable material that is, for example, mounted on a biodegradable, biocompatible material. It will be appreciated that the term "directly" encompasses the use of an adapter molecule to mediate binding of the biologically active ligand to the biocompatible, biodegradable material surface.

It will be appreciated that current forms of inkjet style printing, for example, are only suitable for forming pattern features with a minimum dimension of over 200 μm. This limit arises from limitations on droplet size and the spreading of the printed solution, for example a protein solution. Methods suitable for forming pattern features, with a minimum dimension of less than 200 μm are described below.

It is envisaged that a biodegradable article of the invention may be employed as a tissue regeneration template. On these templates, human or other tissue may be encouraged to grow along the lines (or other pattern) of peptides. The articles of the invention may be used in any organism. It is preferred that the organism is a human and that the article is used in medicine.

The invention employs a nanotechnology approach in which, for example, molecular interactions between the, neurons and the peptide pattern encourage neurite extension. Thus, articles according to particular embodiments of the invention may be beneficial in promoting neurite extension. An article according to a particular embodiment of the invention in which a surface is patterned with hollow tubes of polymer on/in which a biologically active ligand that promotes neurite extension is provided, as described in example 5, may be particularly beneficial in promoting neurite extension.

It will be appreciated that the tissue engineering may be initiated in vivo. For example, cells may be removed from the patient and seeded onto the article (scaffold)in a bioreactor (ie in vitro). When the cells have grown, divided and/or differentiated to form a tissue in the bioreactor, the new tissue may be implanted into the body. It will be appreciated that the article may be implanted at any stage in the growth of the tissue, depending on clinical need. The biodegradable material may be removed by hydrolysis and dissolution in the bioreactor if its function is complete before the engineered tissue is implanted into the patient. Alternatively, the biodegradable tissue may still be present when the tissue is implanted and degradation and/or metabolism may remove the material (or any remaining material after in vitro degradation/metabolism) in vivo. For example, the biodegradable template may be designed to be completely degraded in the bioreactor or it may be designed to provide support to the bioengineered tissue (for example, nerve)for a substantially, predetermined period after surgical implantation. This bioreactor approach is known for use with non-patterned materials for tissue engineering applications (Langer & Vacanti (1993) *Science* 260, 920–926), for example cartilage tissue formation. The templates are degraded, for example, by metabolism after the tissue regeneration has occurred. Therefore, once the new human, for example, tissue has formed, the template is removed and only functional tissue remains. The degradation (including metabolism)of the template may start whilst tissue regeneration is taking place, but it is preferred that the template remains substantially intact until tissue regeneration is substantially complete.

Two important examples of tissue engineering applications in which the method may be used are directed nerve regeneration and new blood vessel formation (vasculogenesis). For nerve regeneration applications, patterns composed of the peptide sequence IKVAV (SEQ ID NO:2) may be used to force or at least encourage nerve cell growth to follow predetermined pathways, i.e. between two severed points of a nerve or towards a denerved tissue.

Figure 3:
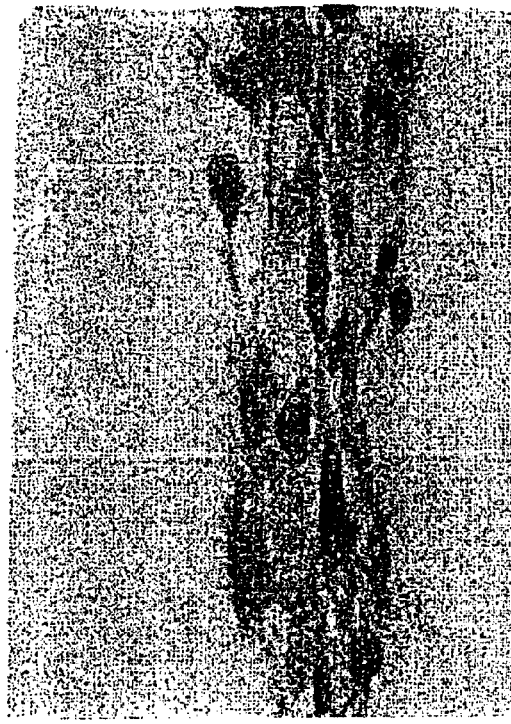
Figure 3:
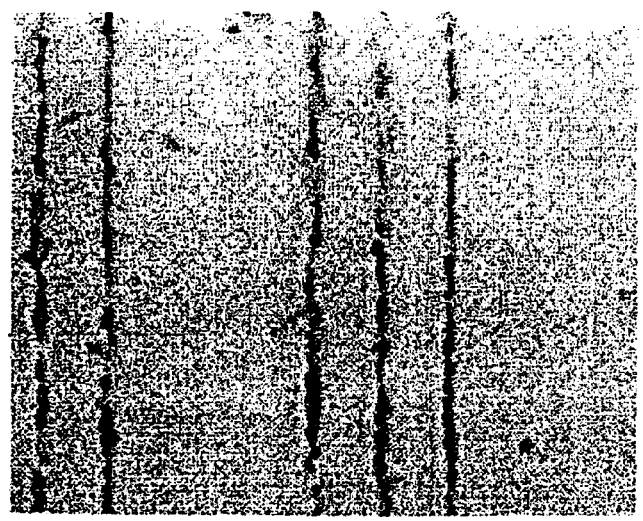
Figure 6:
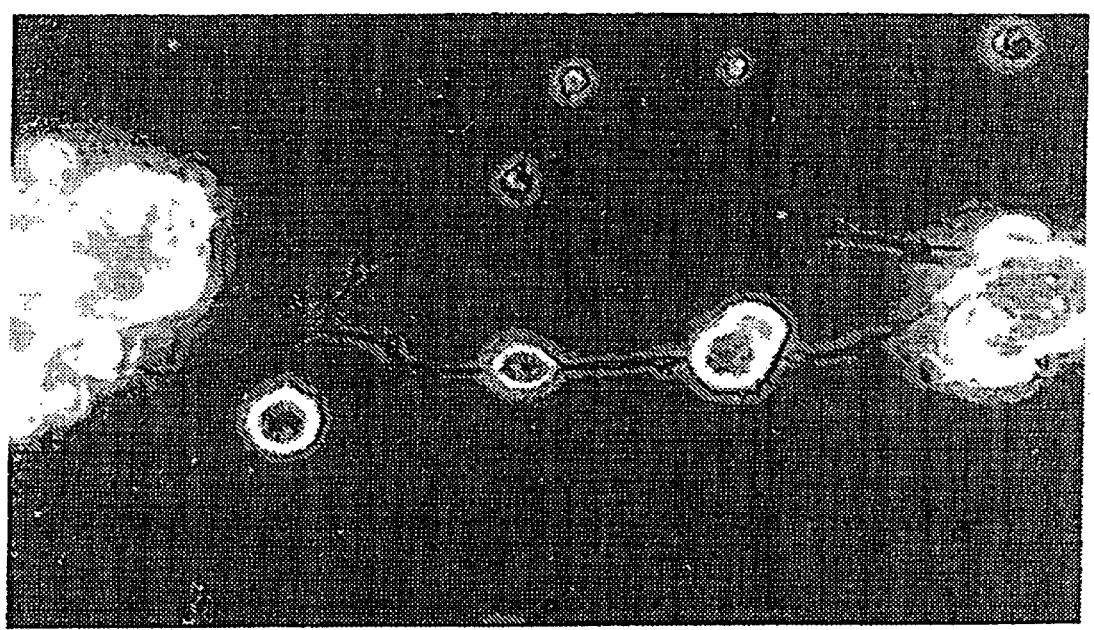

Experimental results have proved that nerve cells adhere and grow along lines generated by the method of the invention (FIGS. 1,2 and 6 and Example 1). For vasculogenesis applications, endothelial cells can be forced to grow along patterns composed of the peptide sequence RGD. Experimental results of directed endothelial cell growth are shown in FIG. 3.

The biodegradable material on which patterns are formed may be based on a material extensively used in clinical applications. After the tissues have been regenerated the material is degraded (which may include metabolism) by the human body and, therefore, is safely removed.

The present invention further provides a process of forming a biodegradable and biocompatible article wherein a spatially controlled pattern of a biologically active ligand is provided on a surface of the said article. The biologically active ligand may be attached to the said surface by means of a specific molecular interaction.

As discussed above, it will be appreciated that, once the said ligand is attached to the said surface in a spatially controlled pattern by means of a specific molecular interaction, a covalent bond may be formed such that the said specific molecular interaction may no longer be required in order for the said ligand to remain attached to the said surface. A method of the invention may be carried out substantially as described below.

1. providing a biodegradable and biocompatible article,
2. providing a means of applying a spatially controlled pattern to a surface of the said article (such that at least one property of the said surface varies over the surface in a substantially predefined manner).
3. forming such a spatially controlled pattern on said surface
4. forming a spatially controlled pattern on said surface of a biologically active ligand.

It will be appreciated that the pattern formed in step 3 may or may not itself be of a biologically active ligand as defined above; however if the pattern is not of a biologically active ligand, the variation in at least one property of the surface must he such as to enable a pattern of a biologically active ligand to be formed on the surface. For example, the property that varies may alter the strength of binding of the biologically active ligand (ligand) to the surface. Preferably the strength of binding is altered such that the ligand is substantially unable to bind to at least one area of the surface and is able to bind in a biologically active amount to at least one other area of the surface.

Thus the following processes are included:

1. The biologically active ligand is able to adhere directly to the surface without treatment of the surface, or an adapter molecule, and is patterned directly onto the surface.

Methods Include a) inkjet style application, wherein a fluid comprising the said ligand is deposited (for example, sprayed) on to the surface, using known techniques.
b) a "rubber stamp" type system, wherein the ligand is, applied to the raised surfaces of a pattern in relief (the stamp) and the stamp is then pressed on to the surface such that at least a proportion of the ligand transferred from the stamp to the surface,
c) a mould system, wherein the mould, when placed on the surface, comprises channels through which a fluid comprising the ligand may flow. For example, the surface may provide one wall and the mould may provide three walls of a channel with a substantially rectangular cross-section.

It will be appreciated that method (a) may only be useful for forming features with a minimum dimension of more than 200$\mu$m, whereas methods (b) and c) may be used to form features that may have a minimum dimension of less than 200$\mu$m, for example typically from 1 $\mu$m to 100 $\mu$m, with a range from 100 nm to 1 mm, as described further below.

2. The biologically active ligand is able to adhere directly to the surface without treatment of the surface, or an adapter molecule but may be prevented from binding to the surface by treatment, for example application of a substance to the surface. The substance may, for example, be a surfactant. The treatment may, for example, be laser treatment.

Methods include a) to c) above, but wherein the: treatment or substance rather than the ligand is applied to the surface to be patterned, and said surface is subsequently contacted with the ligand (which may be achieved using a fluid comprising the ligand)such that the ligand binds substantially only to areas to which the treatment or substance has not been applied.

3. The biologically active ligand is able to adhere directly to the surface only after treatment of the surface. This may be treatment with an adapter molecule which is able to bind to the surface and to the ligand or a treatment, for example doping, which alters the adhesiveness of the surface for the ligand, for example by changing its charge. Preferably an adaptor molecule is used.

Methods include a) to c) above, in which the adapter or treatment is applied to the surface the surface to be patterned, and said surface is subsequently contacted with the ligand (which may be achieved using a fluid comprising the ligand) such that the ligand binds substantially only to areas to which the treatment or substance has been applied
d) laser treatment of the surface may be used.

It is preferred that the ligand is immobilised on the surface by means of a specific molecular interaction, as described above.

It is preferred that the ligand is bound such that the ligand is presented to a cell in a conformation that will allow, for example, a receptor on the cell to bind to the ligand. It is further preferred that the process is of type 3 and that an adapter molecule is used.

It will be appreciated that "inverse patterning" may be used, similar to situation 2 above. For example, a first treatment, or substance may be applied to the surface to be patterned which prevents application of the adapter or second treatment as described in situation 3. The adapter or second treatment is then applied to the surface to be patterned such that the adapter binds, or the second treatment is effective, only in the areas to which the first treatment or substance was not applied.

It will be appreciated that the adapter may comprise more than one component, such that a chain of components links the ligand to the surface. It is preferred that the adapter comprises one component. It is further preferred that the adapter is avidin and that the ligand and article, the surface of which is patterned, comprise biotin.

By fluid is meant a gas or a liquid. Preferably the fluid is a liquid, preferably an aqueous fluid. The ligand or other substance may be dissolved or suspended in the fluid. Preferably the ligand is dissolved in an aqueous fluid.

It is preferred that a mould is used in a process for providing a spatially controlled pattern as described above.

A mould or stamp may be formed from any suitable material. In the following discussion, the term mould is to be taken is covering stamps as well as moulds. It is preferred that the material is elastomeric ie that it is flexible and reversibly deformable. This aids the formation of a pattern of raised and recessed regions in the mould itself and also aids contact of the mould with the surface to be patterned. Preferably the surface of the mould that contacts the surface to he patterned is hydrophobic, but the surface of the mould that forms a channel, as described above, may be hydrophilic. It is preferred that the surface of the mould that forms a channel is hydrophilic. It is preferred that the surface of a stamp is hydrophobic. This may aid formation of a tight contact between the surface and the stamp.

The material may be poly(dimethylsiloxane); PDMS. A mould may be formed by casting a prepolymer of PDMS against a master whose surface has been patterned with a complementary relief structure, for example using photolithography, micromachining or from a commercially available relief structure such as a diffraction grating. These techniques are well known to those skilled in the art, and are described for example in [1] and [12].

It may be more difficult to generate moulds with features less than 1 $\mu$m as the formation of masters with features of this scale may be harder. Methods by which patterns with features of less than 1 $\mu$m may be generated using masters only with features above hum are described in [1]. These methods include deformation of the mould, swelling of the mould with an organic solvent (for example toluene or hexane) or shrinking of a mould formed from prepolymer of PMDS and an inert filler, by extraction of the inert filler, for example with toluene. Suitable fillers include linear, low molecular weight oligomer of PDMS such as silicone fluids PSO39, PSO40, PSO41; Hülls, Piscataway, N.J.

A PDMS mould may be formed from, for example Sylgard 184 (Dow Corning, Midland, Mich., USA), with a ratio between components A and B of 1:10 or 1:20, or PELD 15 (Hülls, Piscataway, N.J.)soft silicone elastomer (ratio of component A and B of 1:10). Component A may be the elastomer and B may be the curing agent. Specific names of the two components may differ between suppliers.

Thus, a patterned poly (dimethyl sisoxane)(PDMS)mould may be formed by curing its prepolymer (Sylgard 184, Dow Coming)on a patterned master prepared photolithographically by exposing and developing a photoresist pattern on gallium/arsenide wafers (12). The PDMS mould bearing the negative pattern of the master may be peeled off and washed repeatedly with ethanol, hexane and deionised water. The mould may be dried under argon prior to plasma etching, as discussed below.

Moulds may be between about 1 cm and 1 mm thick. It is preferred that the aspect ratio (the ratio of the width to the height) of the corrugations is close to unity, preferably between 0.5 and 2. This reduces distortion of the features during patterning of the surface.

Useful dimensions of the mould will be determined by the dimensions of the tissue engineered structure to be produced. The length or width of the mould may be between 100 $\mu$m and 50 cm. Preferably the dimensions of the mould are less that, 10 cm as this may aid preparation and handling. It will be appreciated that an area larger than that of one mould may be patterned by repetitive use of one or more moulds or by sequential or substantially simultaneous use of more than one mould.

Figure 4:
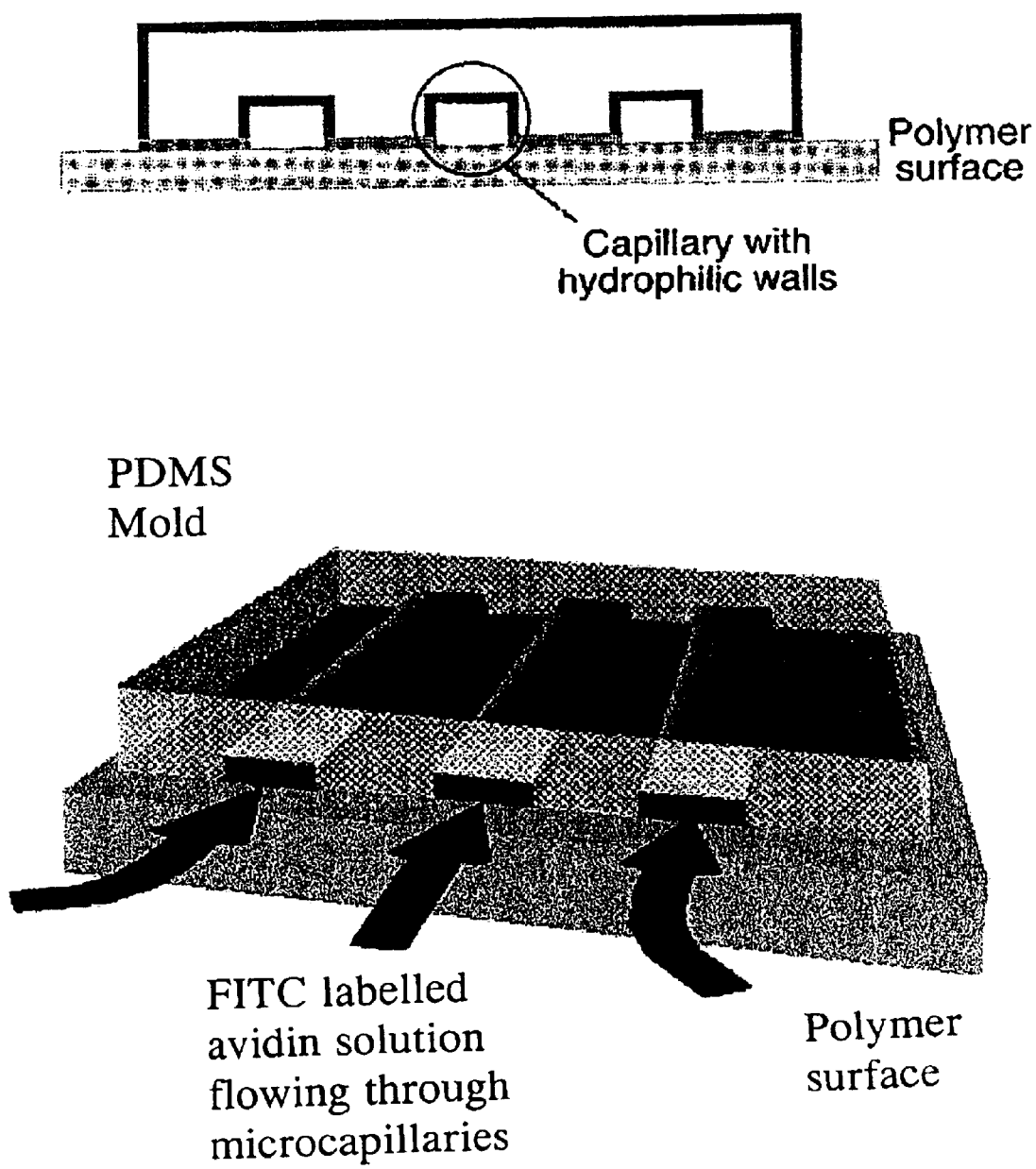
Figure 5:
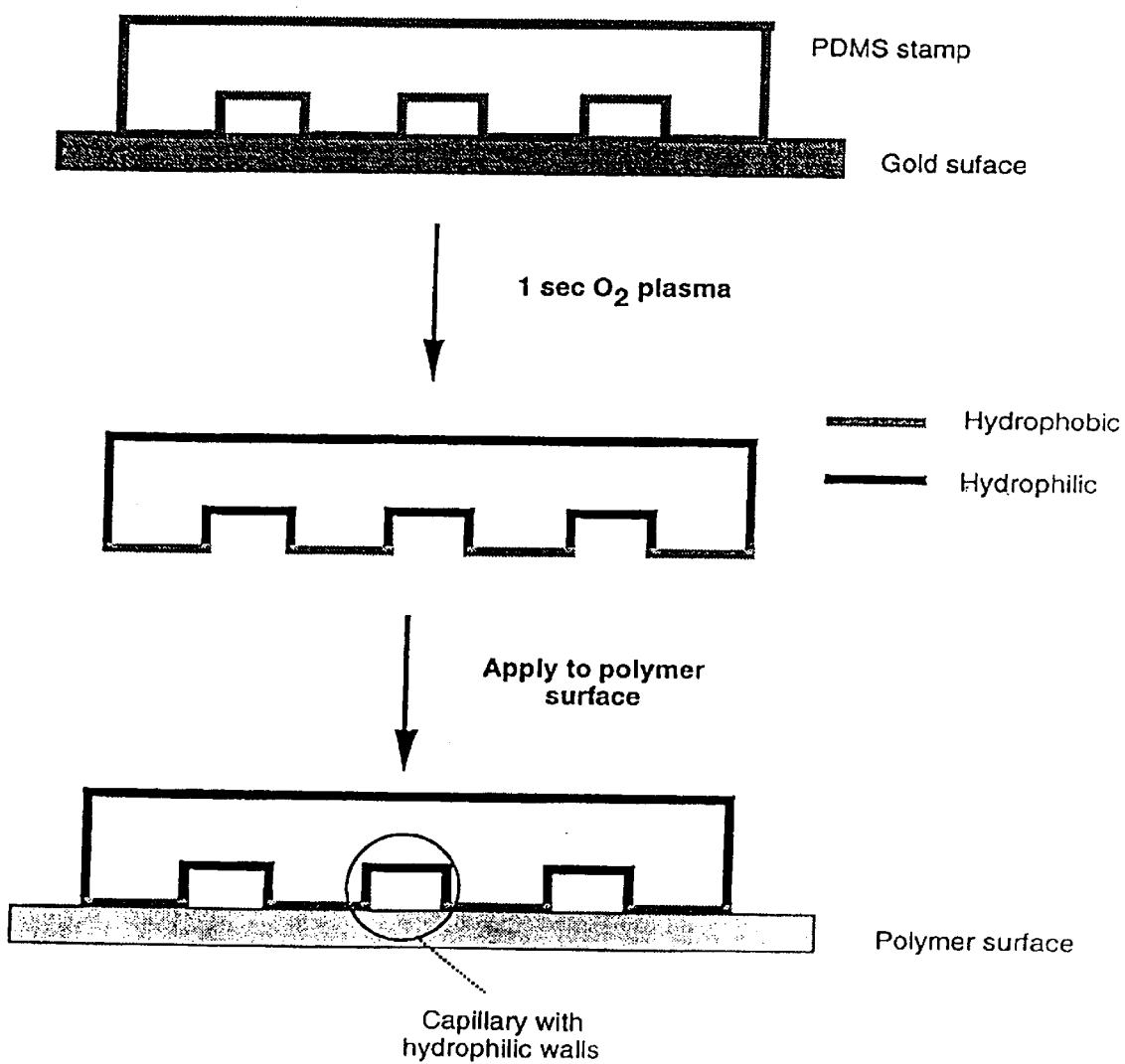

The mould may be selectively plasma etched to create hydrophilic capillary (channel) walls separated by hydrophobic regions (FIGS. 4 and 5). Treatment of the capillary walls whilst protecting other parts of the mould aids entry of an aqueous fluid to the channels whilst retaining hydrophobic regions which aid adherence of the mould to the biodegradable material. If the surface of the mould in contact with the biodegradable material is hydrophilic it may not adhere strongly enough to the material to form the intended pattern.

Once the mould is prepared the following procedure may be followed (shown schematically in FIG. 5).

Following drying under argon, the mould is placed onto an epitaxially grown gold surface (see, for example [12] and Example 1). A tight seal forms between the gold and the protruding areas of the mould. The capillaries are rendered hydrophilic by plasma treatment with $O_2$ (load coil power= 200 W) for 1 s (Bio-Rad RF Plasma Barrel Etcher). The mould is then removed from the gold surface by pealing the surfaces apart. This exposes the protrusions that retain their original hydrophobicity. Contact angle analysis may confirm the differential hydrophobicity/hydrophilicity of shielded and unshielded regions of the mould. Shielded regions may display contact angles of 105° with water, whereas unshielded regions may be saturated with water drops. Further evidence of the successful treatment of the capillary walls may be provided by the rapid flow of water through the capillaries when the mould is placed on a surface.

The mould may be placed on the biodegradable and biocompatible surface to be patterned and a fluid allowed to flow through the channels, as described above. It is preferred that the delay between plasma treatment and use of the mould is minimised. Most preferably, the mould is used within one minute of plasma treatment. Adhesion between the surface to be patterned and the mould may mean that additional pressure is riot required to maintain a tight seal between the surface and the mould. The mould self-seals on the surface. Light pressure (eg tapping with a pair of tweezers) may be applied to ensure that the seal forms. It is desirable that a seal is formed that prevents flow between adjacent, non-communicating channels.

It will be appreciated that the mould may be reused several times and may be plasma treated before each use.

The fluid may for example comprise the biologically active ligand, an adapter molecule, or a substance, such as a surfactant, that prevents binding of the ligand or adapter to the surface to be patterned.

The fluid may be drawn along the channels by capillary action. The fluid (for example avidin solution) may be applied as a drop on the biodegradable surface in such a way that the liquid wets the edge of the mould and can enter the channels. An excess of the fluid is used to avoid depletion of the ligand/substance. The volume of the capillaries is likely to be very low. The biologically active ligand, adapter molecule, or substance, such as a surfactant is patterned in the channel regions. For example, the avidin (adapter molecule) may bind to exposed biotin molecules and, therefore be patterned in the channel regions.

The surface may be washed as follows. Excess fluid comprising the biologically active ligand may be removed by blotting. The surface is washed with the mould in place by immersing the sample in 20 ml of water. The water is removed and optionally the sample dried by flowing argon over the surface of polymer. This washing is repeated 5 times at least. Then, a further 20 ml (for example)of water is added to immerse the polymer surface and mould, and the mould is peeled off the polymer surface. The surface may then be washed with an additional 100 ml of water. The surface may also be washed by removing the mould whilst the mould and surface are immersed in wash buffer, for example water.

If an adapter or "inverse patterning" substance is used, the ligand, which comprises the tag if an adapter is used, may then be added as an aqueous solution without the mould present (i.e. the final patterning step is carried out without the mould and is dependent on the previous patterning step).

For example, if a biotin/avidin/biotin anchor/adapter/tag system is used, the surface is washed and exposed to biotinylated ligand (for example, RGD or IKVAV (SEQ ID NO:2)). This ligand couples with the avidin to form a pattern of the ligand on the surface. A full protocol is given in Example 1.

An alternative method of patterning may be used, for example to pattern avidin on to PLA-PEG-biotin. This method involves patterning a "protecting agent" (typically a pluronic polymer or any other biomedical surfactant) on to the polymer surface. This surfactant pattern blocks avidin binding to the biotinylated polymer on the patterned areas only. The polymer surface with patterned surfactant can be immersed in a solution of the biotinylated ligand to produce an inverse pattern. An inverse pattern is shown in Appendix 4 and a protocol for this procedure is given in Example 2.

An advantage of the "protecting agent" method may be that it is easier to pattern the surfactant than an aqueous avidin solution, in part because stamping procedures can be used. This is because of the physical properties of the surfactant, for example the viscosity. The "protecting agent" method may facilitate the formation of more complex patterns than the protocol given in Example 1. Furthermore, the time required to fabricate patterned surfaces may be shorter.

The protecting agent can be any organic or inorganic molecule that can physically adsorb to the surface of the polymer and thereby block the binding of the adapter to the anchor. The protecting 'agent may create a physical barrier between the anchor and the adapter. The barrier may be a hydrophilic layer of polymer chains that may repel adapter molecules due to an entropic barrier. The protecting agent may be a continuous film that completely covers the underlying polymer surface. More preferably, the protecting agent can be a polymer with surface active activity (termed a polymer surfactant). The polymer surface may include but not be limited to a poly(ethylene glycol)-poly(propylene glycol)-poly(ethylene glycol) block copolymer (for example a Pluronic such as Pluronic F127). "Pluronic" is a registered trademark.

It will be appreciated that a method using a stamp may be used for a liquid comprising an adapter molecule or ligand providing that the liquid has the right properties. The suitability of a liquid for use with a stamping technique may be determined by visualisation of the pattern formed by stamping: if the pattern of the stamp is not reproduced with acceptable precision on the surface then the liquid is unsuitable for patterning using this technique.

It will be appreciated that the liquid should adhere to the polymer surface. The adhesion must be strong enough to maintain the liquid layer for the length of time required to attach the adapter molecule or a ligand or protecting agent as appropriate to the polymer surface, for example the length of time required to attach avidin to non-protected parts of the polymer surface when the liquid is a protecting agent.

The pattern may be visualised by using a label molecule, for example a fluorescent marker. FITC (fluorescein isothiocyanate) is a fluorescent marker that allows the immobilized avidin to be visualised on the biodegradable, biocompatible material surface. Rhodamine may also be used; for example, rhodamine-labelled avaidin (av-R; Sigma, Dorset, UK). Attachment of a biotinylated ligand is still possible with the FITC or rhodamine present. However, it will be appreciated that in a product for medical use it may be preferred that the FITC is omitted. It will be appreciated that this or a related method of visualisation may be used with any of the patterning techniques described above, and may be used, for example, to assess the sharpness of boundaries of pattern features produced using different techniques.

Constraints on the pattern produced, by the flow method (ie using a mould) are that the pattern must be continuous from the point of entry of the fluid (for example, solution of an adapter molecule) into the capillary to the point of exit. For the protecting agent method (ie using a stamp) the pattern complexity is determined by the complexity of the polydimethylsiloxane stamp. This has been discussed by Whitesides in [1] and in Kumar et al (1994) *Langmuir* 10, 1498–1511 [12].

It will be appreciated that a further aspect of the invention is a biodegradable and biocompatible article having a surface wherein an adapter compound, which is attached to the surface by binding to an anchor molecule provided on the surface, is provided on said surface in a spatially controlled pattern, wherein the said adapter molecule is suitable for attaching a biologically active ligand to the surface by means of a specific molecular interaction. It will be appreciated that such an article may be an intermediate in the preparation of an article according to the first aspect of the invention. Such an intermediate may be prepared and stored, for example so that the biologically active ligand may be bound to the adapter immediately prior to use. This may be beneficial, for example if the biologically active ligand is labile. Preferences for this aspect of the invention are as for the first aspect of the invention, described above.

A further aspect of the invention is a kit comprising said biodegradable and biocompatible article and the said biologically active ligand. It will be appreciated that the said biologically active ligand may comprise a tag, as described above.

Multiple patterning can be achieved by more than one addition of adapter. After each addition a tagged ligand is immobilized. In general, useful combinations may include cell adhesive ligands that are specific for unique cell types. For example, galactose-terminated polyethylene glycol chains bind hepatocytes whilst RGD-containing sequences bind virtually all cell types. Therefore, hepatocytes can patterned onto surfaces and then surrounded by endothelial cells. This can encourage cell-to-cell contacts that are thought to be vital in ensuring that hepatocytes function successfully.

Cells that adhere to parts of the surface which do not have adhesion promoting ligands attached may tend to undergo apoptosis (pre-programmed cell death).

Binding of albumin or other proteins, for example constituents of tissue fluid, may mask the cell adhesive ligands and therefore prevent cell adhesion. However, the hydrophilicity of the surface may be selected or manipulated to minimize albumin (or other protein) non-specific adsorption.

Apoptosis may occur in vivo on non-ligand presenting surfaces of the biodegradable substrate as long as those surfaces are not coated with plasma proteins (eg fibronectin or laminin) due to a normal physiological process. Coating with plasma proteins is minimised by the presence of PEG chains on the surface of a polymer, for example PLA-PEG-biotin. Control of protein binding in non-patterned areas may he well-controlled on such polymers.

A number of proteins (eg disintegrins)and peptides prevent cell adhesion. These may be patterned onto a surface as described above. It will be appreciated that complementary patterns of adhesion-promoting and adhesion-preventing ligands may be applied to a surface in order, for example, to provide enhanced control of cellular adhesiveness and/or differentiation.

It is envisaged that growth factors may be impregnated into the polymer rather than immobilized on the surface. This may facilitate release of the growth factor into the surrounding medium, where it may be maximally active. The method of the invention may be used in the area of spatially controlled nerve regeneration. A number of companies are currently developing technologies to stimulate nerve regrowth after injury, but these do not involve spatially controlling this growth. Companies such as Neurogenesis Inc. have developed new nerve growth factors that promote neurite extension from damaged nerves. Ciliary neurotrophic factor may be used. The biodegradable templates of the invention which may comprise such nerve growth factors may guide neurite extension along patterned lines and the templates may release the nerve growth factors (using conventional controlled release mechanisms during polymer degradation; see for example [11]) over extended time periods.

The articles and methods of the invention may also be used to accelerate wound healing. Patterned templates may encourage keratinocytes to migrate into wound areas by stimulating integrin mediated cell migration along lines of RGD peptide. Again, growth factors may be released from the templates to stimulate wound healing.

In addition, the invention may be used for tissue engineering applications including vasculogenesis, hepatic regeneration (which may include vasculogenesis) and ligament formation.

The invention will now be described, by way of example, by reference to the following figures and Examples.

FIGURES

FIG. 1: Fluorescence images of patterned surfaces

FIG. 2: Diagram of patterned cell lines on a biodegradable surface

FIG. 3: Images of directed endothelial cell growth

FIG. 4: Hydrophilic and hydrophobic regions of the mould. The mould is placed on the biodegradable surface, for example PLA-PEG-biotin surface and adapter (for example avidin) solution flows through the hydrophilic channels. The adapter may be labelled, for example with a fluorescent molecule, so that the pattern may be visualised.

FIG. 5: Selective plasma etching of the mould. A patterning technique may require treatment of the PDMS mould with an $O_2$, plasma. This treatment increases the hydrophobicity of any PDMS surface that is not protected by the gold surface. Transferring the treated mould to the PLA-PEG-biotin surfaces produces capillaries with hydrophilic walls. Avidin solution flow across the PLA-PEG-biotin surface is restricted to the capillary regions by the hydrophobic regions of the mould base.

FIG. 6: PC12 nerve cells on a 70 $\mu$m wide line with neurites joining the cells together.

Figure 7:
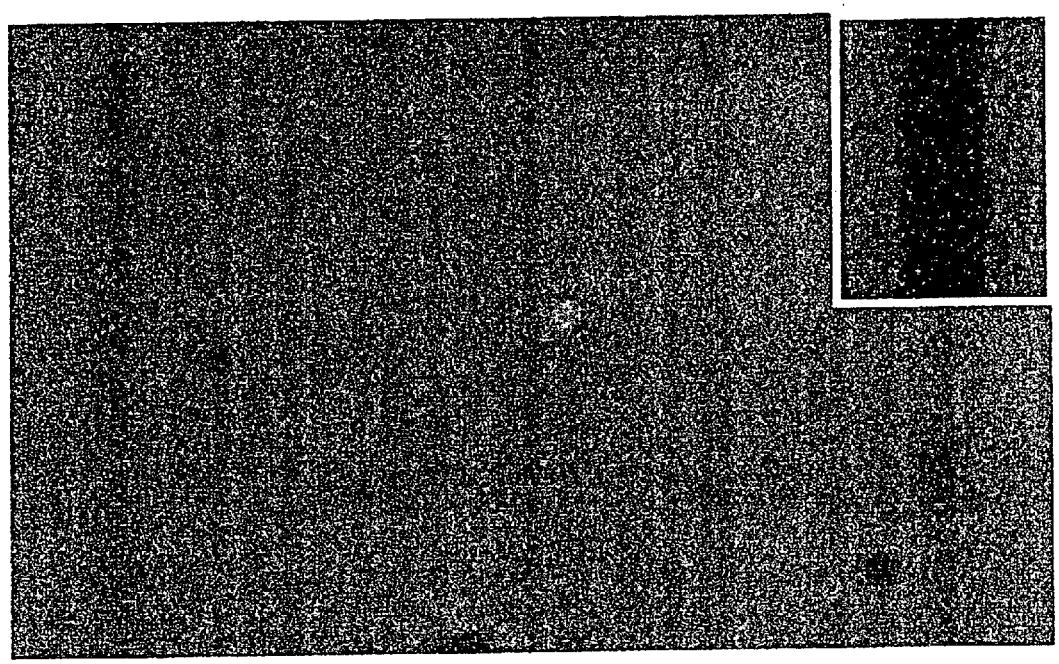

FIG. 7: An inverse pattern of fluorescent (FITC) labelled avidin.

Figure 8:
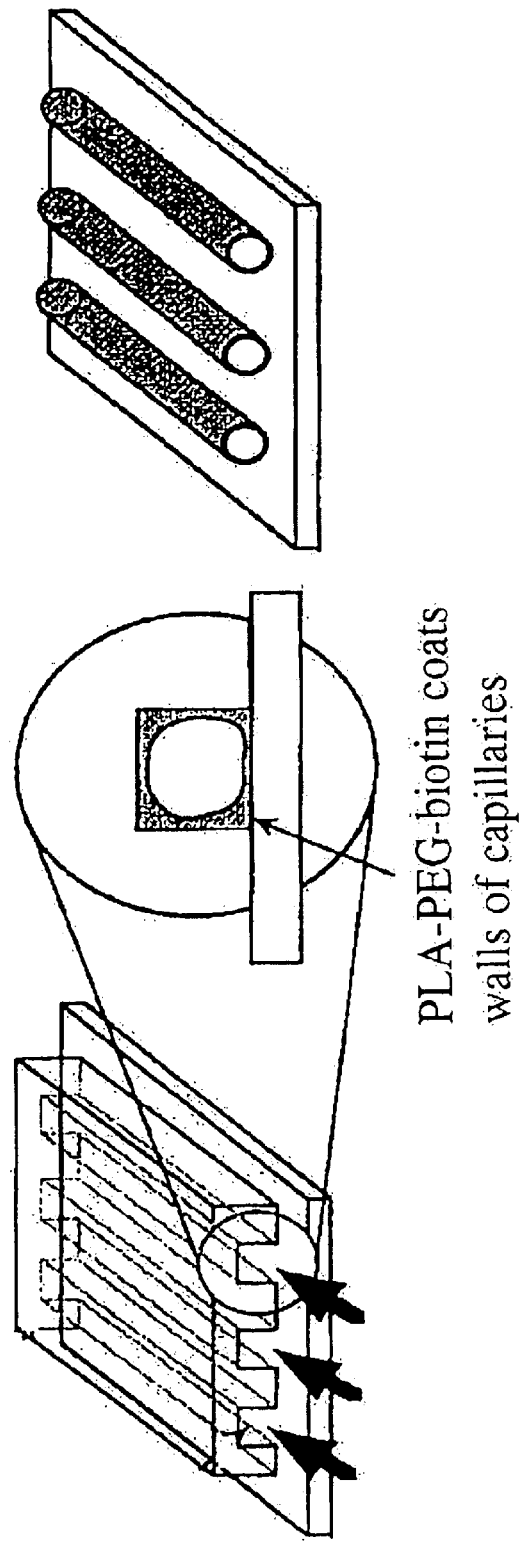

FIG. 8: A method of forming tubes or rods of a material, for example a biodegradable, biocompatible material, on a surface. A PDMS mould is placed on a polymer surface. A volatile solution of a material or example a polymer, such as PLA-PEG-biotin, is flowed through the mould channels. The material coats the walls of the channels to form rods or hollow tubes. The PDMS mould is removed. Not all steps are shown; further steps may be required as described below when using a PDMS mould. A biologically active ligand may be bound to the tubes or rods, for example via an avidin adapter. The tubes or rods may be used to guide cell growth, for example nerve regeneration, either with or without coating with a biologically active ligand.

Figure 9:
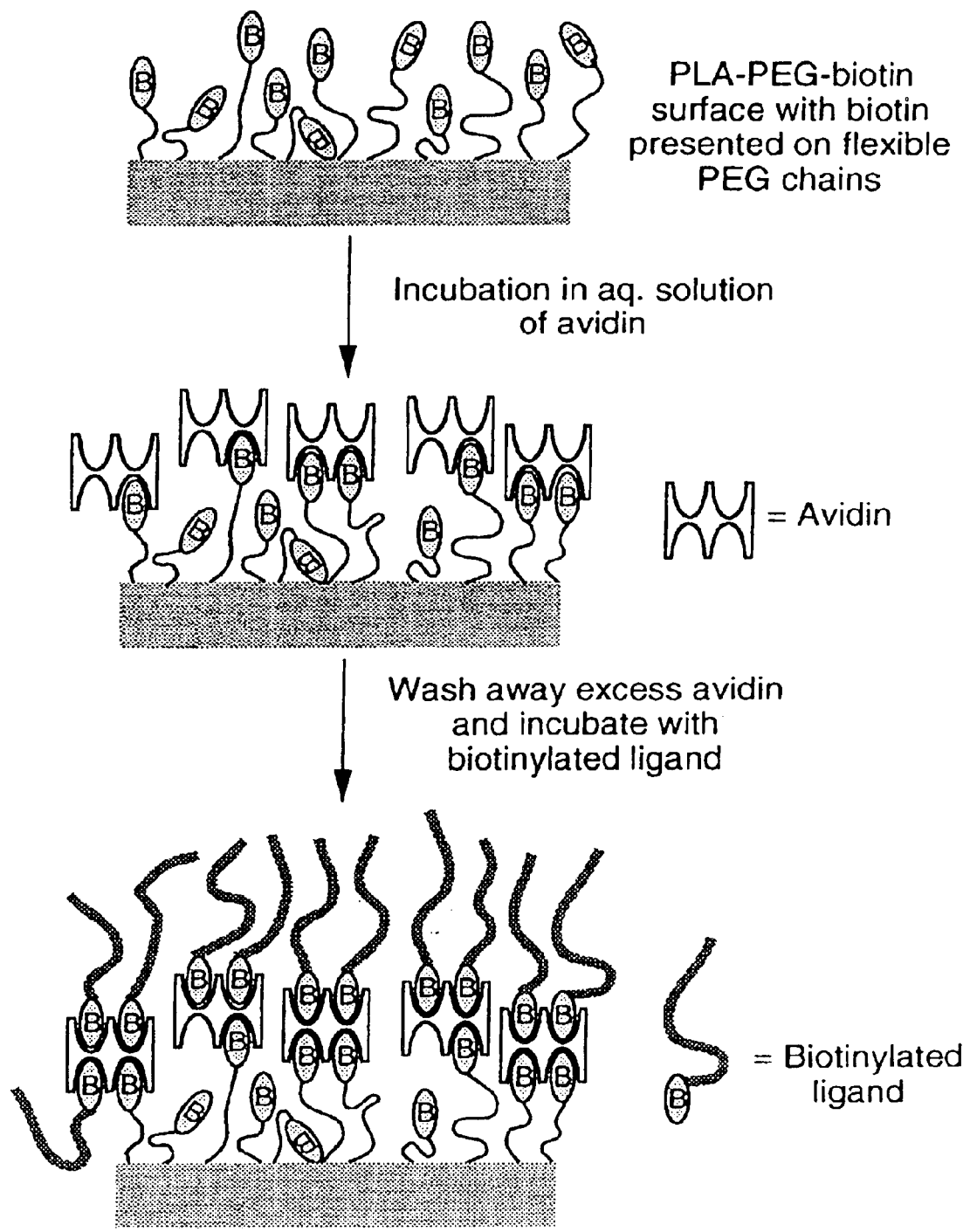

FIG. 9: Schematic representation of the surface engineering of PLA-PEG biotin. Biotin moieties presented at the polymer surface are used to immobilise tetrameric avidin molecules. Free biotin binding sites on the avidin molecules are in turn used to anchor biotinylated ligands. All steps in the surface engineering are performed in aqueous environments.

Figure 10:
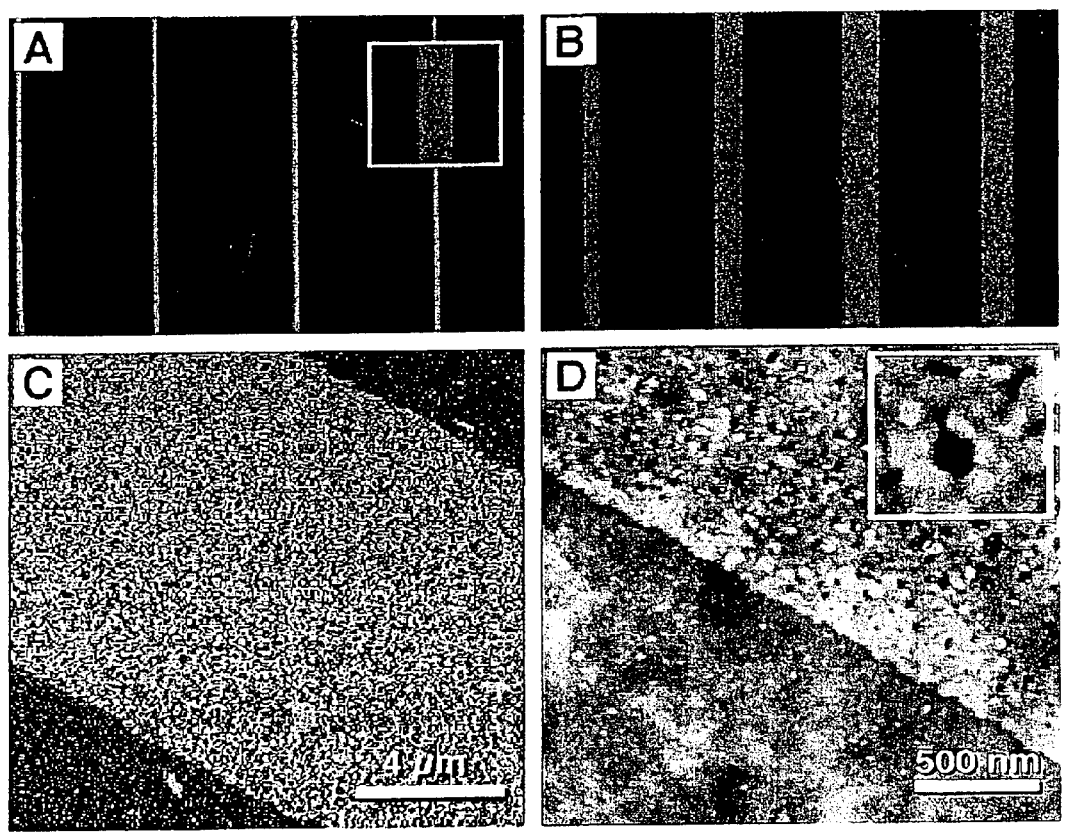

FIG. 10: A)Fluorescence microscopy image of 12 $\mu$m-wide lines of av-R on a PLA-PEG-biotin surface. The image was recorded at 10×magnification. Inset shows a region of the patterned surface at 60×magnification. B) Fluorescence microscopy image of 30, 50, 70 and 70 $\mu$m-wide lines of av-R on a PLA-PEG-biotin surface (10× magnification). C) Phase detection AFM (atomic force microscopy) image of a line confirming the generation of a sharp pattern edge. D) Tapping mode AFM image of boundary between avidin covered lines and PLA-PEG-biotin only gap regions. The inset shows a 100nm×100 nm region of the line displaying individual molecules of the avidin.

Figure 11:
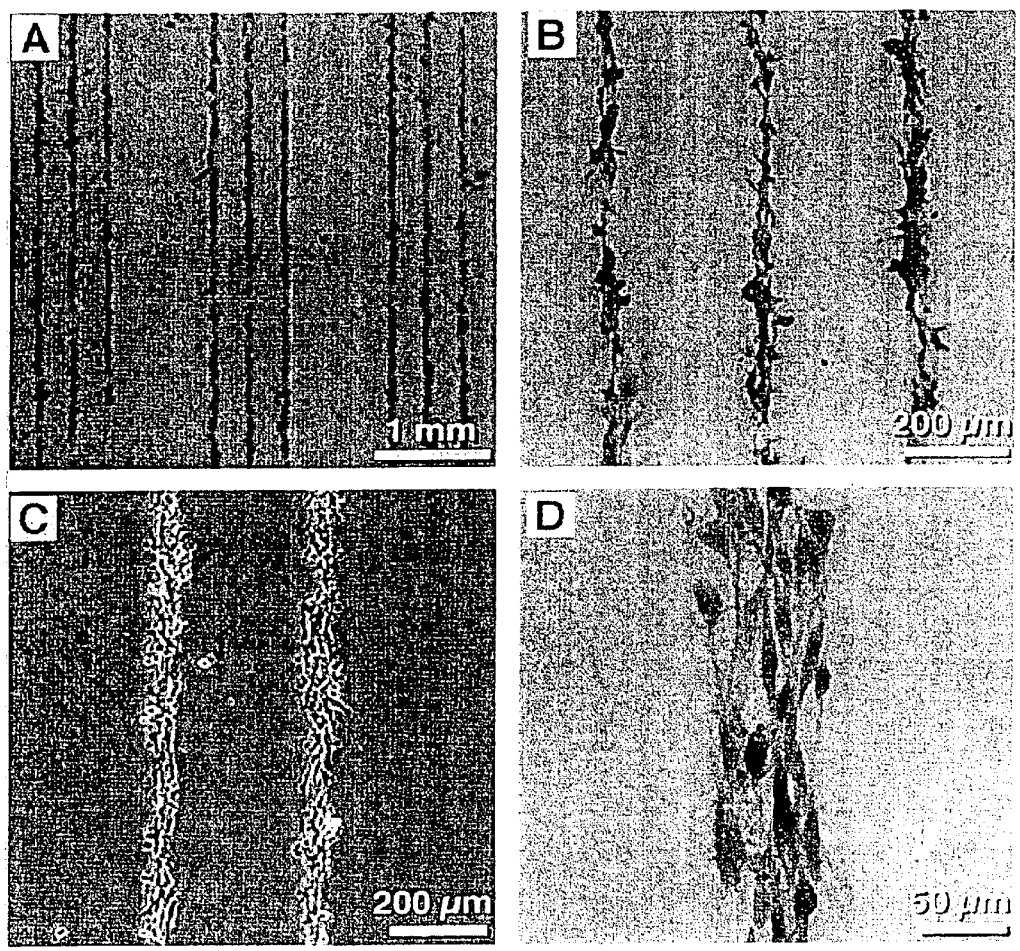

FIG. 11: Spatially controlled adhesion and spreading of biovine aortic endothelial cells on 70 and 50 $\mu$m-wide lines containing RGD peptides. Panels A, B, D are transmission images. Panel C is a phase contrast image.

Figure 12:
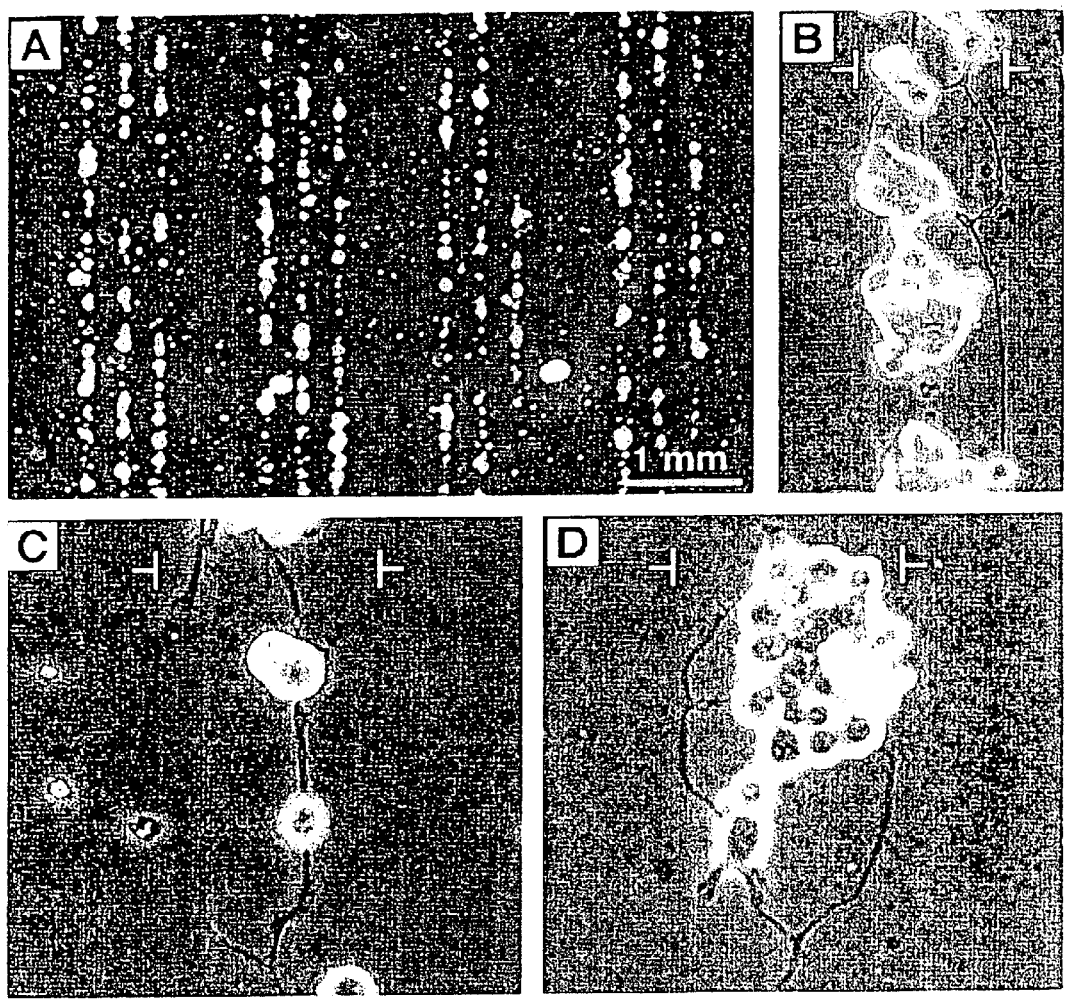

FIG. 12: Spatially controlled adhesion and spreading of PC12 cells on lines containing IKVAV (SEQ ID NO:2) peptides recorded by phase contrast light microscopy. A) Low magnification image showing the preferential adhesion of PC12 cells to the 70 and 50 $\mu$m-wide lines. B, C) Images showing neurite extension and joining between individual PC12 cells and cell clusters. White markers indicate the boundaries of the 70 $\mu$m lines. No neurites were observed to extend from any PC12 cells that adhered on nonpatterned regions. D) The path of the neurite extending up the left-hand boundar of the line is altered by the IKVAV (SEQ ID NO:2) peptide pattern restricting the neurite to the line.

EXAMPLES

Example 1

Preparation of a Pattern of a Cell Adhesive Peptide Ligand

Step 1—-Preparation of PLA-PEG-biotin

Stir α-amine co-hydroxy PEG (100 mmol) with N-hydroxysuccinimide-biotin (500 mmol) and triethylamine (500 mmol) in dichloromethane (typically 10 ml) and acetonitrile (typically 10 ml) at room temperature under argon overnight. Isolate the biotinylated PEG by vacuum filtration, and dried from toluene azeotrope. Secondly, polymerize (l-)lactide from the ω-hydroxy PEG-biotin in refluxing toluene, optionally using stannous 2-ethylhexanoate as a catalyst to give PLA-PEG-biotin. The weight of (l)-lactide and ω-hydroxy PEG-biotin is determined by the required ratio of block molecular weights. The final polymeric material is recovered by dissolution in dichloromethane and precipitation in cold ether, for example by addition of cold ether.

Step 2—Preparation of PLA-PEG biotin Films

Dissolve approximately 1 mg to 5 mg of polymer into 5 ml of trifluoroethanol (TFE). Pour- the resulting solution into a polystyrene petri dish and dry off the TFE under vacuum.

Step 3—Preparation of the Polydimethylsiloxane (PDMS) Mould

The PDMS mould is prepared using standard published procedures [1, 12]. The mould may be formed by curing its prepolymer, for example Sylgard 184, Dow Coming, on a patterned master prepared photolithographically by exposing and developing a photoresist pattern on gallium/arsenide wafers. A gold substrate is prepared using a standard published procedure (DeRose, J. A., Thundat, T., Nagahara, L. A., Lindsay, S. M., *Surf. Sci.* (1991), 256, 102) involving the thermo-evaporation of gold onto a freshly cleaved mica surface to generate an epitaxially grown gold surface. The PDMS mould bearing the negative pattern of the master is peeled off and washed with ethanol or repeatedly with ethanol, hexane and deionised water and then dried under a stream of argon gas. The mould is then placed on the gold surface in such a way that the channels in the mould form enclosed capillaries (as shown in FIG. 5).

A tight seal will form between the gold and the protruding areas of the mould. The capillaries are then rendered hydrophilic by plasma treatment with $O_2$ (load coil power=200 W) for 1 s (Bio-Rad RF Plasma Barrel Etcher). The mould is then removed from the gold surface by pealing the surfaces apart. This exposes the protrusions that retained their original hydrophobicity.

Step 4—Patterning of Avidin Onto the PLA-PEG-biotin Surface

Within 1 minute, the mould is placed on the PLA-PEG-biotin surface in such a way that the hydrophobic protrusions contact the polymer surface. Light pressure may be employed to ensure that the mould seals with the PLA-PEG-biotin surface.

Then 2 ml of a 1 mg/ml avidin solution (aq) is dropped onto the PLA-PEG-biotin surface in such a way that the liquid wets the edge of PDMS mould and can enter the capillaries. Alternatively, for example, approximately 1 ml of a 500 µg/ml solution of rhodamine-labelled avidin in distilled water may be used.

After one hour the solution may be removed by blotting and the sample is washed by immersing in 20 ml of water and left for 1 to 5 minutes. Then, the water is removed and optionally the sample dried by placing in a stream of argon gas for 10 minutes. The drying procedure is extended if liquid remains in the channel after this time. This washing procedure is repeated 5 times.

Then, a further 20 ml of water is poured onto the PLA-PEG-biotin and then mould is removed by peeling with tweezers to separate the PDMS and PLA-PEG-biotin surfaces.

After removal of the mould, the PLA-PEG-biotin surface is rinsed with approximately 100 ml of water.

Step 5—Immobilization of the Cell-adhesive Peptide Ligand

A cell-adhesive peptide ligand with the C or N terminus biotinylated may be synthesized using standard solid-state peptide synthesis procedures. The solucation may be sterilised under UV light for 10 minutes. An aqueous solution of the biotinylated peptide is prepared at 1 mg of peptide per ml, or in which the molar concentration of biotin is approximately 1 mmol. 10 ml of this solution is added to the patterned surface generated in Step 4. After a 10 minute incubation period or 30 minutes at 37° C. on a shaker plate the peptide solution is removed. The polymer surface is then washed with 100 ml of water or with aliquots of phosphate buffered saline (PBS).

Example 2

Preparation of a Pattern of a Cell Adhesive Peptide Ligand (Method 2)

Steps 1 to 3 are carried out as described in Example 1.

Step 4—Patterning of Pluronic F127 onto PLA-PEG-biotin

Within 1 minute, the mould is placed on the PLA-PEG-biotin surface in such a way that the hydrophobic protrusions contact the polymer surface. Light pressure may be employed to ensure that the mould seals with the PLA-PEG-biotin surface.

An aqueous solution of Pluronic F127 (500 µg/ml) is prepared. Then 2 ml of this solution (aqueous) is dropped onto the PLA-PEG-biotin surface in such a way that the liquid wets the edge of PDMS mould and can enter the capillaries.

After one hour the sample is washed by immersing in 20 ml of water and left for 1 minute. Then, the water is removed by and the sample dried by placing in a stream of argon gas for 10 minutes. The drying procedure is extended if liquid remains in the channels after this time. This washing procedure is repeated 5 times.

Then, a further 20 ml of water is poured onto the PLA-PEG-biotin and then the mould is removed by peeling with tweezers to separate the PDMS and PLA-PEG-biotin surfaces.

After removal of the mould, the PLA-PEG-biotin surface is rinsed with approximate 100 ml of water.

Step 5—Patterning of Avidin Onto the PLA-PEG-biotin Surface 10 ml of a 1 mg/ml aqueous solution of avidin is poured onto the Pluronic patterned PLA-PEG-biotin surface. After 10 minutes all free biotin at the polymer surface will have coupled to avidin molecules. The avidin solution is then removed and the polymer surface is washed with 100 ml of water.

Step 6—Immobilization of the Cell-adhesive Peptide Land

A cell-adhesive peptide ligand with the C or N terminus biotinylated is synthesized using standard solid-state peptide synthesis procedures. An aqueous solution of the biotmylated peptide is prepared in which the molar concentration of biotin is approximately 1 mmol. 10 ml of this solution is added to the patterned surface generated in Step 4. After a 10 minute incubation period the peptide solution is removed. The polymer surface is then washed with 100 ml of water.

An example of an "inverse pattern" is shown in FIG. 7.

Example 3

Regeneration of Neurons Following Nerve Severance or Damage

One of the mechanisms by which a peripheral nerve cell retains viability within the body is via the retrograde transport of nerve growth factor (NGF) from the terminus of a neuron to the cell body. When a nerve cell is damaged the cell body is deprived of NGF and cell death can occur if the supply of the factor is not rapidly restored.

The formation of line patterns of peptide incorporating the IKVAV (SEQ ID NO:2) sequence provides a method of rapidly restoring neurite extensions and, hence, restoring NGF retrograde movement.

Following the severance or damage of a nerve biomaterials composed of PLA-PEG-biotin are inserted on which IKVAV (SEQ ID NO:2) peptide sequences are patterned in lines running from one severed end to the other. Alternatively, the biomaterial can run from a damaged nerve to a tissue. The effect of having the IKVAV (SEQ ID NO:2) peptide pattern present is to stimulate neurite extension and to guide the growth of these neurites towards their target. This guidance effectively shortens the average growth required to get the neurite to the target.

After the nerve has reformed the biodegradable nature of the polymer ensures its removal from the site of nerve regeneration.

Example 4

Ex vivo Bioengineering of Human Nervous Tissue Using Patterned Surfaces of Biodegradable Templates In a number of tissue engineering applications, involving non-patterned surfaces, a functional tissue is grown on a biodegradable template within a bioreactor. Then, when partially or fully grown, the tissue-template construct is surgically implanted into the body. Examples of this type of tissue engineering are provided by Langer and Vacanti (Langer R & Vacanti JP (1993) *Science* 260, 920–926).

Using biodegradable templates with patterned surfaces, fabricated using the invented technology, this type of tissue engineering is extended to tissue types that possess spatially controlled distributions of cells. In the treatment of a severed nerve, a bioreactor strategy is employed in which a template is prepared with a lined pattern that presents IKVAV (SEQ. ID NO:2)-containing peptides. Nerve cells and any required supporting cell (eg Schwann cells) are then grown within the template tube in the presence of growth factors. After a predetermined culturing period the nerve cell-template construct is surgically inserted into the region of nerve damage.

The biodegradable template may be designed to be completely degraded in the bioreactor or it may be designed to provide support to the bioengineered nerve tissue for a predetermined period after surgical implantation.

Example 5

Formation of Tubes or Rods for Guiding Cell Growth or Tissue Regeneration

Tubes or rods of a material, for example a biodegradable, biocompatible material, may be formed on a surface using a mould, for example a PDMS mould, as shown in FIG. 8. A PDMS mould is placed on a polymer surface. A volatile solution of a material, for example a polymer, such as PLA-PEG-biotin, is flowed through the mould channels. The material coats the walls of the channels to form rods or hollow tubes, which may have an external diameter between about 1 μm and about 1 mm. The material may be PLA-PEG-biotin. Following removal of the mould, a biologically active ligand may be bound to the tubes or rods, for example via an avidin adapter, for example, if using PLA-PEG-biotin. The tubes or rods may be used to guide cell growth, for example nerve regeneration, either with or without coating with a biologically active ligaud. A suitable biologically active ligand for use in encouraging nerve regeneration may be nerve growth factor or a peptide comprising a IKVAV (SEQ ID NO:2) peptide sequence.

Example 6

Cell Spreading Experiment

A patterned polymer surface is prepared as described in Example 1;

Bovine aortic endothelial cells (BAECs) were maintained in low glucose Dulbecco's modifed Eagle's medium (DMEM) supplemented with 10% fetal bovine serum, 0.5% penicillin, 0.5% streptomycin and 1% L-glutamine in a humidified incubator at 37° C. and 5% $CO_2$. Cells were passaged by trypsinisation before reaching confluence, usually every fifth day. Fresh media were added every other day. PC12 cells (ATCC CRL 1721) were grown in suspension culture in F-12K media supplemented with 15% horse serum, 2.5% fetal bovein serum, 0.5% penicillin, 0.5% streptomycin and 1% L-glutamine in a humidified incubator at 37° C. and 5% $CO_2$. Cells were passaged 1:5 every third day. All cell culture reagents were obtained from Sigma unless otherwise stated.

BAECs between passages 7 and 9 were removed from tissue culture flasks by trypsinisation, pelleted by centrifugation, resuspended, washed three times and diluted to the appropriate concentration in serum-free MDEM. PC12 cells were primed with culture medium containing 50 ng/ml 7S nerve growth factor (NGF) 48 h prior to the experiment. The cells were pelleted by centrifugation, washed three times with serum-free F-12K medium, passed through a 22-guage needle to obtain a single cell suspension, and diluted to the appropriate concentration with serum-free. F-12K medium supplemented with 50ng/ml 7S NGF. For both cell types, approximately 10,000 cells/$cm^2$ were added to each sample and the plates returned to the incubator for the duration of the experiment (48hr). At the end point of the experiment, the samples were washed gently with PBS to remove unattached cells and visualised with a Nikon Diaphot TMD inverted microscope equipped with a Hitachi HV-C20 high resolution CCD video camera using phase contrast objectives. Images were digitised using NIH Image (v1.61) image analysis software. In addition, some BAEC samples were fixed in 10% neutral buffered formalin for 10 min, washed with water, and stained with hematoxylin for visualisation.

Images are shown in FIGS. 11 and 12. The BAECs adhered and spread on the RGD-functionalised (biotin-$G_{11}$ GRGDS (SEQ ID NO:18)) lines but did not adhere to unfunctionalised areas between the lines. Complete cell coverage of the 70 and 50 μm width lines was achieved, but little cell adhesion occurred to the 30 or 12 μm-wide lines.

As shown in FIG. 12, PC12 cells showed selective adherence to the IKVAV functionalised lines (biotin-$G_5$CSRARKQAASIKVAVSADR (SEQ ID NO:19), with only a small degree of cell adhesion between the lines. In addition, no cell adhesion was observed on negative control samples consisting of PLA-PEG-biotin-avidin patterns in the absence of the biotinylated IKVAV (SEQ ID NO:2) sequence. Directionally controlled neurite outgrowth was stimulated by the IKVAV (SEQ ID NO:2) micropattern, with neurites extending between groups of cells often hundreds of microns apart (FIGS. 12B, C). The extent of control over neurite growth was demonstrated by the morphology of many neurites that approached the boundary between the functionalised and unfunctionalised surfaces but were always effectively restricted from crossing the interface (FIG. 12D).

Example 7

Atomic Force Microscopy images were obtained as described in the Figure legends using a Digital Instruments (Santa Barbara, Calif., US) multimode scanning probe microscope with a Digital Instruments Nanoscope IIIa controller. Images were acquired in tapping mode using sharpened silicon nitride tips with cantilever resonance frequencies in the range of 307–375 kHz. Simultaneous topographic and phase images were obtained at a scan rate of 1 Hz. In phase detection AFM, differences in viscoelastic and adhesive properties of avidin and PLA_PEG-biotin generate image contrast (Tamayo & Garcia (1996) *Langmuir* 12, 4450–4455).

The thickness of the avidin layer deposited on the PLA-PEG-biontin was measured by tapping mode AFM. The AFM image in FIG. 10D shows the topography of a PLA-PEG-biotin surface at a protein boundary. The edge of the line was resolved, and cross-sectional analysis recorded a step height of less than 10 nm. Given that the dimensions of the avidin molecule have been estimated as 5.6 nm×5.0nm× 4.0 nm by X-ray crystallography (Pugliesi et al (1993) *J Mol Biol* 231, 698–710), a step height of 5 nm is indicative of a monolayer coverage. The insert shows a 100 nm×100 nm scan of the channel on which molecular-resolution of the protein has been achieved. On some areas of the avidin channel protein aggregates are evident. These aggregates were resistant to washing with water. The AFM image in FIG. 10D also demonstrates the exceptional continuity of avidin distribution along the channel edge. Lateral deviations of this edge from a straight line are small. The largest Lateral deviation on this image is 30 nm, equivalent to approximately 6 avidin molecules. Most deviations were found to be less than 20 nm in length.

References

1. Extending microcontact printing as a microlithographic technique. Xia Y, Whitesides G M. *Lanmuir* 1997; 13: 2059–2067
2. Using self-assembled monolayers to understand the interactions of man-made Surfaces with proteins and cells. Mrksich M, Whitesides G M, *Annual Review of Biophysics and Biomolecular Structure* 1996; 25:55–78
3. Spattially controlled adhesion, spreading, and differentiation of endothelial cells on self assembled molecular monolayers. Spargo et al (1994) *PAS USA* 91, 11070-1 1074
4. Patterned delivery of immunoglobulins to surfaces using microfluidic networks. Delamarche E, Bernard A, Schmid H, Michel B, Biebuyck H. *Science* 1997;276:179781
5. Biomaterials of Tissue Engineering. Hubbell J A. *Bio/technology* 1995; 13:565–576
6. 1994 Whittaker Lecture—Polymers for drug delivery and tissue engineering, Langer R, *Annals of Biomedical Engineering* 1995;23: 101–111
7. Bronzino J D. *The Biomedical Engineering Handbook.* Boca Raton, Fla., 1995
8. A new plasma-based method to promote cell adhesion on micrometric tracks on polystyrene substrates. Lhoest J-B, Detrait E, Dewez J-L, Van den Bosch de Aguilar P, Bertrand P. *Journal of Biomaterial Science. Polymer Edition* 1996;7:1039–1054
9. Neuronal cell attachment to fluorinated ethylene propylene films with covalently immobilized laminin oligopeptides YIGSR and IKVAV. Ranieri J P, Bellarnkonda R, Bekos E T, Vargo T G, Gardella J A, Aebischer P. *Journal of Biomedical Materials Research* 1995; 29:779–785
10. Stimulation of neurite outgrowth using an electrically conducting polymer. Schmidt C E, Shastri V R, Vacanti J P., Langer R, *PNAS USA* 1997;94:8948–8953
11. Jantzen & Robinson (1996) "Sustained- and Controlled-release drug delivery systems" in "*Modern Pharmaceutics*" 3rd edition, editors Banker & Rhodes, Marcel Dekker, Inc., New York, Basel, Hong Kong.
12. Kumar et al (1994) "Patterning self-assembled monolayers: applications in materials science" *Lanmuir* 10, 1498–1511.

We claim:

1. A biodegradable and biocompatible article comprising a biologically active ligand bound to the surface of said biodegradable and biocompatible article in a spatially controlled pattern,
   wherein the biologically active ligand is attached to the surface via a specific molecular interacton with an adapter compound, the adapter compound being attached to the surface by means of aspecific molecular interaction with an anchor molecule provided on the surface of the article, and
   wherein the specific molecular interaction has a Kd between $10^{-10}$ and $10^{-17}$ M.

2. The article of claim 1 wherein the specific molecular interaction has a $K_d$ between $10^{-13}$ and $10^{-16}$ M.

3. The article of claim 1 wherein the specific molecular interaction is selected from the group consisting of an interaction between biotin and avidin and an interaction between biotin and streptavidin.

4. The article of claim 1 wherein a dimension of a feature of the spatially controlled pattern is selected from the group consisting of being less than or equal to about 200 μm and less than or equal to about 100 μm.

5. The article of claim 1 wherein the ligand is selected from the group consisting of a nerve, epithelial growth factor and a peptide that may stimulate neurite growth.

6. The article of claim 3 wherein the ligand and anchor molecule comprises biotin and the adapter compound is selected from the group consisting of avidin and streptavidin.

7. The article of claim 1 wherein the ligand is a molecule that can be attached to a biotin molecule.

8. The article of claim 1 comprising a biodegradable and biocompatible polymer selected from the group consisting of polyesters, poly(orthoester)s, polyanhydrides, poly(amino acid)s, poly(pseudo amino acid)s, and polyphosphazenes.

9. The article of claim 8 wherein the polyester is selected from the group consisting of poly(lactic acid)s, poly(glycolic acid)s, copolymers of lactic and glycolic acid, copolymers of lactic and glycolic acid with poly(ethylene glycol), poly(ε-caprolactone)s, poly(3-hydroxybutyrate)s, poly(p-dioxanone)s and poly(propylene fumarate)s.

10. The article of claim 8 wherein the polymer comprises biotin.

11. The article of claim 10 wherein the polymer is polylactic acid-poly(ethylene glycol)-biotin (PLA-PEG-biotin).

12. The article of claim 1 wherein the spatially controlled pattern is selected from the group consisting of parallel lines and branched lines.

13. The article of claim 12 wherein the branched lines form a tree pattern.

14. The article of claim 1 wherein a dimension of a feature of the spatially controlled pattern is selected from the group consisting of dimensions being less than or equal to about 1 mm, 200 μm, 100 μm, 10 μm, 1 μm, and 100 nm.

15. The article of claim 1 wherein a dimension of a feature of the spatially controlled pattern is selected from the group consisting of dimensions being less than or equal to about 90 μm, 80 μm, 70 μm, 60 μm, 50 μm, 40 μm, 30 μm, 20 μm, 10 μm, 1 μm, 500 nm and 100 nm.

16. The article of claim 1 wherein the biologically active ligand affects cell adhesion or differentiation.

17. The article of claim 1 wherein the ligand is selected from the group consisting of peptides, proteins, carbohydrates, nucleic acids, lipids, polysaccharides, and combinations thereof.

18. The article of claim 1 wherein the ligand binds a cell via a cell adhesion receptor.

19. The article of claim 18 wherein the cell adhesion receptor is an integrin.

20. The article of claim 5 wherein the ligand is a peptide selected from the group consisting of the sequences IKVAV (SEQ ID NO:2), RNIAEIIKDA (SEQ ID NO:9) and CSRARKQAASIKVAVSADR (SEQ ID NO:3).

21. The article of claim 1 wherein the ligand can be released from the biodegradable article during tissue regeneration.

22. The article of claim 1 further comprising a biologically active molecule that is not patterned on the surface.

23. The article of claim 22 wherein the biologically active molecule that is not patterned is released as the article or part thereof is degraded.

24. The article of claim 1 wherein more than one type of biologically active ligand is immobilised.

25. The article of claim 1 wherein the biologically active ligand inhibits cell adhesion or differentiation.

26. The article of claim 25 wherein the biologically active ligand that inhibits cell adhesion is patterned with a ligand that promotes cell adhesion.

27. The article of claim 1 which is suitable for spatially organising cell adhesion and/or cell differentiation.

28. The article of claim 1 which is suitable for use in forming functional tissue.

29. The article of claim 28 wherein after functional tissue has formed the article is removed by natural metabolism.

30. A process of forming a biodegradable and biocompatible article comprising, providing on a surface of an article a biologically active ligand in a spatially controlled pattern, wherein the biologically active ligand is attached to the surface via a specific molecular interaction with an adapter compound, the adapter compound being attached to the surface by means of a specific molecular interaction with an anchor molecule provided on the surface of the article, and wherein the specific molecular interaction has a Kd between $10^{-10}$ and $10^{-17}$ M.

31. The process of claim 30 wherein the spatially controlled pattern is provided on the surface of the article using a mould or stamp with a spatially controlled pattern of raised regions and recessed regions.

32. The process of claim 31 wherein the mould or stamp comprises an elastomeric material.

33. The process of claim 32 wherein the elastomeric material is poly(dimethyl siloxane) (PDMS).

34. The process of claim 30 comprising the steps of (a) providing a biodegradable and biocompatible article, (b) providing a means for applying a spatially controlled pattern to a surface of the article such that at least one property of the surface varies over the surface in a substantially predefined manner, (c) forming a spatially controlled pattern on a surface of the article such that at least one property of the surface varies over the surface in a predefined manner, and (d) forming a spatially controlled pattern of a biologically active ligand on the surface.

35. The process of claim 34 wherein the pattern formed in step (c) is of the biologically active ligand such that steps (c) and (d) are performed together.

36. The process of claim 34 wherein the means for applying the pattern is an inkjet style printer and step (c) is carried out by an inkjet style printing method.

37. The process of claim 34 wherein the means for applying the pattern comprises a mould having patterned channels comprising a spatially controlled pattern of raised regions and recessed regions, wherein step (c) comprises placing the mould on the surface and allowing a fluid comprising a compound that binds to the ligand to flow through the channels, such that the compound binds to the surface, and wherein step (d) comprises exposing the surface to a ligand such that the ligand binds to the compound.

38. The process of claim 37 wherein the compound is an adapter compound which binds to the surface via an anchor molecule provided on the surface.

39. The process of claim 37 wherein the ligand comprises biotin and the compound is selected from the group consisting of avidin and streptavidin.

40. An article made by the process of claim 30.

41. A method of guiding tissue growth in vitro or in vivo comprising employing the biodegradable and biocompatible article of claim 1 as a tissue engineering template.

42. A method of treating a patient in need of tissue regeneration or of a tissue engineering template comprising administering to the patient the biodegradable and biocompatible article of claim 1.

43. The method of claim 42 wherein the type of tissue regeneration is selected from the group consisting of nerve regeneration, endothelial cell growth, vasculogenesis and wound repair.

44. A biodegradable and biocompatible article having a surface wherein an adapter compound, which is attached to the s&surface by binding by means of a specific molecular interaction to an anchor molecule provided on the surface, is provided on the surface in a spatially controlled pattern, wherein the adapter molecule is suitable for attaching a biologically active ligand to the surface via the adapter molecule by means of a specific molecular interaction between the adapter molecule and the biologically active ligand, and wherein the specific molecular interaction has a Kd between $10^{-10}$ and $10^{-17}$M.

45. The article of claim 8 wherein the article comprises biotin.

46. The article of claim 1 wherein the ligand is selected from the group consisting of a synthetic molecule, an inorganic molecule, and an organic molecule.

47. The article of claim 17 wherein the ligand is a proteoglycan.

* * * * *

UNITED STATES PATENT AND TRADEMARK OFFICE
CERTIFICATE OF CORRECTION

| | | |
|---|---|---|
| PATENT NO. | : 6,855,329 B1 | |
| APPLICATION NO. | : 09/600502 | |
| DATED | : February 15, 2005 | |
| INVENTOR(S) | : Kevin Shakesheff et al. | |

It is certified that error appears in the above-identified patent and that said Letters Patent is hereby corrected as shown below:

Claim 1, column 15, line 39, replace "aspecific" with --a specific--.
Claim 44, column 36, line 36, replace "s&surface" with --surface--.

Signed and Sealed this

Eighteenth Day of September, 2007

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 1

Tyr Ile Gly Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 2

Ile Lys Val Ala Val
1               5

<210> SEQ ID NO 3
<211> LENGTH: 19
<212> TYPE: PRT
<213> ORGANISM: Artificial Sequence
```

```
<220> FEATURE:
<223> OTHER INFORMATION: Description of Artificial Sequence:
      proteoglycan binding domain sequence

<400> SEQUENCE: 3

Cys Ser Arg Ala Arg Lys Gln Ala Ala Ser Ile Lys Val Ala Val Ser
  1               5                  10                  15

Ala Asp Arg

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 4

Arg Glu Asp Val
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 5

Arg Gly Asp Ser
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 6

Arg Gly Asp Val
  1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 7

Leu Arg Gly Asp Asn
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 8

Pro Asp Ser Gly Arg
```

-continued

```
<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 9

Arg Asn Ile Ala Glu Ile Ile Lys Asp Ala
 1               5                   10

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 10

Arg Gly Asp Thr
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: cell
      binding domain sequence

<400> SEQUENCE: 11

Asp Gly Glu Ala
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: cell
      binding domain sequence
<220> FEATURE:
<221> NAME/KEY: MISC_FEATURE
<222> LOCATION: (3)..(3)
<223> OTHER INFORMATION: a hydrophobic amino acid

<400> SEQUENCE: 12

Val Thr Xaa Gly
 1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:
      proteoglycan binding domain sequence
<220> FEATURE:
<221> NAME/KEY: MISC_FEATURE
<222> LOCATION: (1)..(1)
<223> OTHER INFORMATION: a hydrophobic amino acid
<220> FEATURE:
<221> NAME/KEY: MISC_FEATURE
<222> LOCATION: (4)..(4)
<223> OTHER INFORMATION: a hydrophobic amino acid
<220> FEATURE:
```

```
<221> NAME/KEY: MISC_FEATURE
<222> LOCATION: (6)..(6)
<223> OTHER INFORMATION: a hydrophobic amino acid

<400> SEQUENCE: 13

Xaa Asx Asx Xaa Asx Xaa
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:
      proteoglycan binding domain sequence

<400> SEQUENCE: 14

Pro Arg Arg Ala Arg Val
 1               5

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence:
      proteoglycan binding domain sequence

<400> SEQUENCE: 15

Tyr Glu Lys Pro Gly Ser Pro Pro Arg Glu Val Val Pro Arg Pro Arg
 1               5                  10                  15

Pro Gly Val

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence:
      proteoglycan binding domain sequence

<400> SEQUENCE: 16

Arg Pro Ser Leu Ala Lys Lys Gln Arg Phe Arg His Arg Asn Arg Lys
 1               5                  10                  15

Gly Tyr Arg Ser Gln Arg Gly His Ser Arg Gly Arg
                20                  25

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence:
      proteoglycan binding domain sequence

<400> SEQUENCE: 17

Arg Ile Gln Asn Leu Leu Lys Ile Thr Asn Leu Arg Ile Lys Phe Val
 1               5                  10                  15

Lys

<210> SEQ ID NO 18
<211> LENGTH: 16
<212> TYPE: PRT
<213> ORGANISM: Artificial Sequence
<220> FEATURE:
<221> NAME/KEY: MOD_RES
```

-continued

```
<222> LOCATION: (1)
<223> OTHER INFORMATION: biotinylated at position 1
<220> FEATURE:
<223> OTHER INFORMATION: Description of Artificial Sequence: binding
      peptide

<400> SEQUENCE: 18

Gly Gly Gly Gly Gly Gly Gly Gly Gly Gly Gly Gly Arg Gly Asp Ser
 1               5                  10                  15

<210> SEQ ID NO 19
<211> LENGTH: 24
<212> TYPE: PRT
<213> ORGANISM: Artificial Sequence
<220> FEATURE:
<221> NAME/KEY: MOD_RES
<222> LOCATION: (1)
<223> OTHER INFORMATION: biotinylated at position 1
<220> FEATURE:
<223> OTHER INFORMATION: Description of Artificial Sequence: binding
      peptide

<400> SEQUENCE: 19

Gly Gly Gly Gly Gly Cys Ser Arg Ala Arg Lys Gln Ala Ala Ser Ile
 1               5                  10                  15

Lys Val Ala Val Ser Ala Asp Arg
                20
```